(12) United States Patent
Bonadio et al.

(10) Patent No.: US 8,734,336 B2
(45) Date of Patent: May 27, 2014

(54) WOUND RETRACTOR DEVICE

(75) Inventors: Frank Bonadio, Bray (IE); Trevor Vaugh, Birr (IE); John Butler, Blackrock (IE)

(73) Assignee: Atropos Limited, Wicklow (IE)

( * ) Notice: Subject to any disclaimer, the term of this patent is extended or adjusted under 35 U.S.C. 154(b) by 373 days.

(21) Appl. No.: 12/428,823

(22) Filed: Apr. 23, 2009

(65) Prior Publication Data

US 2009/0292176 A1 Nov. 26, 2009

Related U.S. Application Data

(63) Continuation of application No. 11/086,661, filed on Mar. 23, 2005, now Pat. No. 7,537,564, which is a continuation-in-part of application No. 10/995,117, filed on Nov. 24, 2004, now Pat. No. 7,300,399, which is a continuation of application No. 10/133,979, filed on Apr. 29, 2002, now Pat. No. 6,846,287, which is a continuation of application No. 09/801,826, filed on Mar. 9, 2001, now abandoned, which is a continuation of application No. PCT/IE99/00122, filed on Dec. 1, 1999.

(60) Provisional application No. 60/555,398, filed on Mar. 23, 2004.

(30) Foreign Application Priority Data

Dec. 1, 1998 (IE) .......................................... 980997
Feb. 15, 1999 (IE) .......................................... 990111

(51) Int. Cl.
*A61B 1/32* (2006.01)

(52) U.S. Cl.
USPC .......................................... 600/208; 600/203

(58) Field of Classification Search
USPC .......................... 600/201–246; 604/171–180
See application file for complete search history.

(56) References Cited

U.S. PATENT DOCUMENTS

| | | |
|---|---|---|
| 1,157,202 A | 10/1915 | McLeland |
| 1,598,284 A | 8/1926 | Kinney |
| 1,810,466 A | 6/1931 | Deutsch |

(Continued)

FOREIGN PATENT DOCUMENTS

| | | |
|---|---|---|
| DE | 37 39 532 | 12/1988 |
| DE | 37 37 121 | 5/1989 |

(Continued)

OTHER PUBLICATIONS

Kagaya, "Laparoscopic cholecystectomy via two ports, using the 'Twin-Port' system", J. Hepatobiliary Pancreat Surg (2001) 8:76-80.

*Primary Examiner* — Jerry Cumberledge
*Assistant Examiner* — Nicholas Plionis
(74) *Attorney, Agent, or Firm* — Bookoff McAndrews, PLLC

(57) ABSTRACT

A wound retractor device comprises a distal member for insertion into a wound opening, a proximal member for location externally of the wound opening, a connecting member extending at least between the distal member and the proximal member. At least part of the connecting member is movable relative to the proximal member to shorten the length of the connecting member located between the distal member and the proximal member and thereby retract laterally the sides of the wound opening. At least part of the connecting member is movable relative to the proximal member by a guide slot through which the connecting member changes its direction to substantially perpendicular to the longitudinal axis of the wound retractor device.

11 Claims, 14 Drawing Sheets

(56) References Cited

U.S. PATENT DOCUMENTS

| | | |
|---|---|---|
| 2,219,564 A | 10/1940 | Reyniers |
| 2,305,289 A | 12/1942 | Coburg |
| 2,695,608 A | 11/1954 | Gibbon |
| 2,835,253 A | 5/1958 | Borgeson |
| 2,853,075 A | 10/1958 | Hoffman |
| 3,039,468 A | 6/1962 | Price |
| 3,111,943 A | 11/1963 | Orndorff |
| 3,244,169 A | 4/1966 | Baxter |
| 3,253,594 A | 5/1966 | Matthews et al. |
| 3,313,299 A | 4/1967 | Spademan |
| 3,329,390 A | 7/1967 | Hulsey |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,447,533 A | 6/1969 | Spicer |
| 3,522,800 A | 8/1970 | Lesser |
| 3,523,534 A | 8/1970 | Nolan |
| 3,570,475 A | 3/1971 | Weinstein |
| 3,592,198 A | 7/1971 | Evans |
| 3,656,485 A | 4/1972 | Robertson |
| 3,685,786 A | 8/1972 | Woodson |
| 3,717,151 A | 2/1973 | Collett |
| 3,729,006 A | 4/1973 | Wilder et al. |
| 3,782,370 A | 1/1974 | McDonald |
| 3,797,478 A | 3/1974 | Walsh et al. |
| 3,807,393 A | 4/1974 | McDonald |
| 3,828,764 A | 8/1974 | Jones |
| 3,841,332 A | 10/1974 | Treacle |
| 3,853,126 A | 12/1974 | Schulte |
| 3,853,127 A | 12/1974 | Spademan |
| 3,856,021 A | 12/1974 | Mcintosh |
| 3,907,389 A | 9/1975 | Cox et al. |
| 3,915,171 A | 10/1975 | Shermeta |
| 3,965,890 A | 6/1976 | Gauthier |
| 3,996,623 A | 12/1976 | Kaster |
| 3,998,217 A | 12/1976 | Trumbull et al. |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,083,370 A | 4/1978 | Taylor |
| 4,096,853 A | 6/1978 | Weigand |
| 4,130,113 A | 12/1978 | Graham |
| 4,177,814 A | 12/1979 | Knepshield |
| 4,188,945 A | 2/1980 | Wenander |
| 4,217,664 A | 8/1980 | Faso |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,306,562 A | 12/1981 | Osborne |
| 4,321,915 A | 3/1982 | Leighton |
| 4,331,138 A | 5/1982 | Jessen |
| 4,338,934 A | 7/1982 | Spademan |
| 4,338,937 A | 7/1982 | Lehrman |
| 4,367,728 A | 1/1983 | Mutke |
| 4,399,816 A | 8/1983 | Spangler |
| 4,411,659 A | 10/1983 | Jensen et al. |
| 4,421,296 A | 12/1983 | Stephens |
| 4,424,833 A | 1/1984 | Spector |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,485,490 A | 12/1984 | Akers et al. |
| 4,488,877 A | 12/1984 | Klein |
| 4,543,088 A | 9/1985 | Bootman et al. |
| 4,550,713 A | 11/1985 | Hyman |
| 4,553,537 A | 11/1985 | Rosenberg |
| 4,601,710 A | 7/1986 | Moll |
| 4,610,665 A | 9/1986 | Matsumoto |
| 4,626,245 A | 12/1986 | Weinstein |
| 4,634,424 A | 1/1987 | O'Boyle |
| 4,649,904 A | 3/1987 | Krauter |
| 4,654,030 A | 3/1987 | Moll et al. |
| 4,673,393 A | 6/1987 | Suzuki et al. |
| 4,673,394 A | 6/1987 | Fenton |
| 4,755,170 A | 7/1988 | Golden |
| 4,776,843 A | 10/1988 | Martinez et al. |
| 4,777,943 A | 10/1988 | Chvapil |
| 4,784,646 A | 11/1988 | Feingold |
| 4,798,594 A | 1/1989 | Hillstead |
| 4,809,679 A | 3/1989 | Shimonaka |
| 4,863,438 A | 9/1989 | Gauderer |
| 4,889,107 A | 12/1989 | Kaufman |
| 4,895,565 A | 1/1990 | Hillstead |
| 4,897,081 A | 1/1990 | Poirier |
| 4,903,710 A | 2/1990 | Jessamine et al. |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,015,228 A | 5/1991 | Columbus et al. |
| 5,019,101 A | 5/1991 | Purkait |
| 5,026,366 A | 6/1991 | Leckrone |
| 5,041,095 A | 8/1991 | Littrell |
| 5,045,070 A | 9/1991 | Grodecki et al. |
| D320,658 S | 10/1991 | Quigley et al. |
| 5,071,411 A | 12/1991 | Hillstead |
| 5,074,878 A | 12/1991 | Bark et al. |
| 5,082,005 A | 1/1992 | Kaldany |
| 5,086,763 A | 2/1992 | Hathman |
| 5,092,846 A | 3/1992 | Nishijima |
| 5,125,897 A | 6/1992 | Quinn et al. |
| 5,141,498 A | 8/1992 | Christian |
| 5,149,327 A | 9/1992 | Oshiyama |
| 5,156,617 A | 10/1992 | Reid |
| 5,158,553 A | 10/1992 | Berry et al. |
| 5,159,921 A | 11/1992 | Hoover |
| 5,161,773 A | 11/1992 | Tower |
| 5,167,636 A | 12/1992 | Clement |
| 5,178,162 A | 1/1993 | Bose |
| 5,188,595 A | 2/1993 | Jacobi |
| 5,192,301 A | 3/1993 | Kamiya et al. |
| 5,207,656 A | 5/1993 | Kranys |
| 5,209,737 A | 5/1993 | Ritchartt |
| 5,211,370 A | 5/1993 | Powers |
| 5,211,633 A | 5/1993 | Stouder |
| 5,213,114 A | 5/1993 | Bailey, Jr. |
| 5,234,455 A | 8/1993 | Mulhollan |
| 5,242,409 A | 9/1993 | Buelna |
| 5,248,304 A | 9/1993 | Vigdorchik et al. |
| 5,261,883 A | 11/1993 | Hood et al. |
| 5,263,922 A | 11/1993 | Sova et al. |
| 5,269,763 A | 12/1993 | Boehmer |
| 5,269,772 A | 12/1993 | Wilk |
| D343,236 S | 1/1994 | Quigley et al. |
| 5,279,575 A | 1/1994 | Sugarbaker |
| D346,022 S | 4/1994 | Quigley et al. |
| 5,299,582 A | 4/1994 | Potts |
| 5,300,036 A | 4/1994 | Mueller |
| 5,308,336 A | 5/1994 | Hart et al. |
| 5,309,896 A | 5/1994 | Moll et al. |
| 5,316,541 A | 5/1994 | Fischer |
| 5,320,611 A | 6/1994 | Bonutti |
| 5,330,437 A | 7/1994 | Durman |
| 5,330,497 A | 7/1994 | Freitas |
| 5,334,143 A | 8/1994 | Carroll |
| 5,336,192 A | 8/1994 | Palestrant |
| 5,342,315 A | 8/1994 | Rowe et al. |
| 5,342,385 A | 8/1994 | Norelli et al. |
| 5,350,364 A | 9/1994 | Stephens et al. |
| 5,364,345 A | 11/1994 | Lowery et al. |
| 5,366,478 A | 11/1994 | Brinkerhoff et al. |
| 5,368,545 A | 11/1994 | Schaller et al. |
| 5,383,861 A | 1/1995 | Hempel |
| 5,385,553 A | 1/1995 | Hart et al. |
| 5,391,153 A | 2/1995 | Haber et al. |
| 5,391,156 A | 2/1995 | Hildwein et al. |
| 5,395,367 A | 3/1995 | Wilk |
| 5,403,264 A | 4/1995 | Wohlers |

(56) References Cited

U.S. PATENT DOCUMENTS

| | | |
|---|---|---|
| 5,407,433 A | 4/1995 | Loomas |
| 5,423,848 A | 6/1995 | Washizuka et al. |
| 5,429,609 A | 7/1995 | Yoon |
| 5,431,676 A | 7/1995 | Durbal |
| 5,443,452 A | 8/1995 | Hart et al. |
| 5,456,284 A | 10/1995 | Ryan |
| 5,476,475 A | 12/1995 | Gadberry |
| 5,480,410 A | 1/1996 | Cuschieri et al. |
| 5,496,280 A | 3/1996 | Vandenbroeck |
| 5,503,112 A | 4/1996 | Luhman |
| 5,514,109 A | 5/1996 | Mollenauer et al. |
| 5,514,133 A | 5/1996 | Golub et al. |
| 5,520,632 A | 5/1996 | Leveen |
| 5,522,791 A | 6/1996 | Leyva |
| 5,522,824 A | 6/1996 | Ashby |
| 5,524,644 A | 6/1996 | Crook |
| 5,526,536 A | 6/1996 | Cartmill |
| 5,545,179 A | 8/1996 | Williamson, IV |
| 5,562,632 A | 10/1996 | Davila |
| 5,562,688 A | 10/1996 | Riza |
| 5,577,993 A | 11/1996 | Zhu et al. |
| 5,582,577 A | 12/1996 | Lund et al. |
| 5,584,850 A | 12/1996 | Hart et al. |
| 5,601,579 A | 2/1997 | Semertzides |
| 5,620,415 A | 4/1997 | Lucey |
| 5,632,979 A | 5/1997 | Goldberg |
| 5,634,911 A | 6/1997 | Hermann et al. |
| 5,634,936 A | 6/1997 | Linden |
| 5,634,937 A | 6/1997 | Mollenauer et al. |
| 5,636,645 A | 6/1997 | Ou |
| 5,640,977 A | 6/1997 | Leahy et al. |
| 5,649,550 A | 7/1997 | Crook |
| 5,653,705 A | 8/1997 | de la Torre et al. |
| 5,657,963 A | 8/1997 | Hinchliffe |
| 5,658,272 A | 8/1997 | Hasson |
| 5,658,306 A | 8/1997 | Kieturakis |
| 5,672,168 A | 9/1997 | de la Torre et al. |
| 5,685,854 A | 11/1997 | Green |
| 5,707,703 A | 1/1998 | Rothrum et al. |
| 5,709,664 A | 1/1998 | Vandenbroeck |
| 5,720,730 A | 2/1998 | Blake, III |
| 5,738,628 A | 4/1998 | Sierocuk et al. |
| 5,741,234 A | 4/1998 | Aboul-Hosn |
| 5,741,298 A | 4/1998 | MacLeod |
| 5,749,882 A | 5/1998 | Hart et al. |
| 5,755,660 A | 5/1998 | Tyagi |
| 5,769,783 A | 6/1998 | Fowler |
| 5,769,794 A | 6/1998 | Conlan et al. |
| 5,782,812 A | 7/1998 | Hart et al. |
| 5,795,290 A | 8/1998 | Bridges |
| 5,803,919 A | 9/1998 | Hart et al. |
| 5,803,921 A | 9/1998 | Bonadio |
| 5,807,350 A | 9/1998 | Diaz |
| 5,810,721 A | 9/1998 | Mueller et al. |
| 5,813,409 A | 9/1998 | Leahy et al. |
| 5,814,026 A | 9/1998 | Yoon |
| 5,817,062 A | 10/1998 | Flom |
| 5,820,555 A | 10/1998 | Mueller |
| 5,832,925 A | 11/1998 | Rothrum |
| 5,853,395 A | 12/1998 | Crook et al. |
| 5,865,728 A | 2/1999 | Moll et al. |
| 5,871,474 A | 2/1999 | Hermann et al. |
| 5,882,344 A | 3/1999 | Stouder |
| 5,899,208 A | 5/1999 | Bonadio |
| 5,904,703 A | 5/1999 | Gilson |
| 5,906,577 A | 5/1999 | Beane et al. |
| 5,916,232 A | 6/1999 | Hart |
| 5,947,922 A | 9/1999 | MacLeod |
| 5,951,467 A | 9/1999 | Picha et al. |
| 5,957,913 A | 9/1999 | de la Torre et al. |
| 5,964,781 A | 10/1999 | Mollenauer et al. |
| 5,993,485 A | 11/1999 | Beckers |
| 5,994,450 A | 11/1999 | Pearce |
| 5,997,515 A | 12/1999 | de la Torre et al. |
| 6,024,736 A | 2/2000 | de la Torre et al. |
| 6,025,067 A | 2/2000 | Fay |
| 6,033,426 A | 3/2000 | Kaji |
| 6,033,428 A | 3/2000 | Sardella |
| 6,042,573 A | 3/2000 | Lucey |
| 6,048,309 A | 4/2000 | Flom et al. |
| 6,059,816 A | 5/2000 | Moenning |
| 6,077,288 A | 6/2000 | Shimomura et al. |
| 6,099,506 A | 8/2000 | Macoviak et al. |
| 6,110,154 A | 8/2000 | Shimomura et al. |
| 6,123,689 A | 9/2000 | To et al. |
| 6,142,935 A | 11/2000 | Flom et al. |
| 6,142,936 A | 11/2000 | Beane et al. |
| 6,150,608 A | 11/2000 | Wambeke |
| 6,159,182 A | 12/2000 | Davis |
| 6,162,172 A | 12/2000 | Cosgrove et al. |
| 6,162,196 A | 12/2000 | Hart et al. |
| 6,162,206 A | 12/2000 | Bindokas |
| 6,163,949 A | 12/2000 | Neuenschwander |
| 6,164,279 A | 12/2000 | Tweedle |
| 6,171,282 B1 | 1/2001 | Ragsdale |
| 6,183,486 B1 | 2/2001 | Snow et al. |
| 6,238,373 B1 | 5/2001 | de la Torre et al. |
| 6,254,533 B1 | 7/2001 | Fadem et al. |
| 6,254,534 B1 | 7/2001 | Butler et al. |
| 6,258,065 B1 | 7/2001 | Dennis |
| 6,315,770 B1 | 11/2001 | de la Torre et al. |
| 6,319,246 B1 | 11/2001 | de la Torre et al. |
| 6,322,541 B2 | 11/2001 | West |
| 6,346,074 B1 | 2/2002 | Roth |
| 6,382,211 B1 | 5/2002 | Crook |
| 6,420,475 B1 | 7/2002 | Chen |
| 6,440,063 B1 | 8/2002 | Beane |
| 6,450,983 B1 | 9/2002 | Rambo |
| 6,454,783 B1 | 9/2002 | Piskun |
| 6,464,686 B1 | 10/2002 | O'Hara et al. |
| 6,485,435 B1 | 11/2002 | Bakal |
| 6,485,467 B1 | 11/2002 | Crook et al. |
| 6,488,620 B1 | 12/2002 | Segermark et al. |
| 6,533,734 B1 | 3/2003 | Corley, III et al. |
| 6,551,270 B1 | 4/2003 | Bimbo et al. |
| 6,554,793 B1 | 4/2003 | Pauker |
| 6,578,577 B2 | 6/2003 | Bonadio et al. |
| 6,582,364 B2 | 6/2003 | Butler et al. |
| 6,589,167 B1 | 7/2003 | Shimonmura |
| 6,589,211 B1 | 7/2003 | MacLeod |
| 6,607,504 B2 | 8/2003 | Haarala |
| 6,613,952 B2 | 9/2003 | Rambo |
| 6,623,426 B2 | 9/2003 | Bonadio et al. |
| 6,706,050 B1 | 3/2004 | Giannadakis |
| 6,714,298 B2 | 3/2004 | Ryer |
| 6,723,044 B2 | 4/2004 | Pulford |
| 6,793,621 B2 | 9/2004 | Butler et al. |
| 6,796,940 B2 | 9/2004 | Bonadio et al. |
| 6,797,765 B2 | 9/2004 | Pearce |
| 6,814,078 B2 | 11/2004 | Crook |
| 6,814,700 B1 | 11/2004 | Mueller et al. |
| 6,840,951 B2 | 1/2005 | de la Torre et al. |
| 6,846,287 B2 | 1/2005 | Bonadio et al. |
| 6,860,463 B2 | 3/2005 | Hartley |
| 6,866,861 B1 | 3/2005 | Luhman |
| 6,884,253 B1 | 4/2005 | McFarlane |
| 6,902,541 B2 | 6/2005 | McNally et al. |
| 6,908,430 B2 | 6/2005 | Caldwell |
| 6,916,331 B2 | 7/2005 | Mollenauer et al. |
| 6,936,037 B2 | 8/2005 | Bubb |
| 6,939,296 B2 | 9/2005 | Ewers |
| 6,945,932 B1 | 9/2005 | Caldwell et al. |
| 6,958,037 B2 | 10/2005 | Ewers |
| 6,979,324 B2 | 12/2005 | Bybordi |
| 7,008,377 B2 | 3/2006 | Beane |
| 7,052,454 B2 | 5/2006 | Taylor |
| 7,081,089 B2 | 7/2006 | Bonadio et al. |
| 7,118,528 B1 | 10/2006 | Piskun |
| 7,195,590 B2 | 3/2007 | Butler et al. |
| 7,297,106 B2 | 11/2007 | Yamada et al. |
| 7,300,399 B2 | 11/2007 | Bonadio et al. |
| 7,344,547 B2 | 3/2008 | Piskun |
| 7,445,597 B2 | 11/2008 | Butler et al. |
| 7,537,564 B2 | 5/2009 | Bonadio et al. |

(56) References Cited

U.S. PATENT DOCUMENTS

| | | |
|---|---|---|
| 7,540,839 B2 | 6/2009 | Butler et al. |
| 7,559,893 B2 | 7/2009 | Bonadio et al. |
| 7,749,415 B2 | 7/2010 | Brustad et al. |
| 7,867,164 B2 | 1/2011 | Butler et al. |
| 7,998,068 B2 | 8/2011 | Bonadio et al. |
| 8,012,088 B2 | 9/2011 | Butler et al. |
| 8,021,296 B2 | 9/2011 | Bonadio et al. |
| 8,157,817 B2 | 4/2012 | Bonadio et al. |
| 8,187,178 B2 | 5/2012 | Bonadio et al. |
| 8,317,691 B2 | 11/2012 | Bonadio et al. |
| 8,375,955 B2 | 2/2013 | Desai et al. |
| 2001/0037053 A1 | 11/2001 | Bonadio et al. |
| 2001/0039430 A1 | 11/2001 | Dubrul et al. |
| 2001/0047188 A1 | 11/2001 | Bonadio et al. |
| 2002/0002324 A1 | 1/2002 | Mcmanus |
| 2002/0010389 A1 | 1/2002 | Butler et al. |
| 2002/0038077 A1 | 3/2002 | de la Torre et al. |
| 2002/0072762 A1 | 6/2002 | Bonadio et al. |
| 2002/0111536 A1 | 8/2002 | Cuschieri et al. |
| 2003/0028179 A1 | 2/2003 | Piskun |
| 2003/0078478 A1 | 4/2003 | Bonadio et al. |
| 2003/0139756 A1 | 7/2003 | Brustad |
| 2003/0187376 A1 | 10/2003 | Rambo |
| 2003/0192553 A1 | 10/2003 | Rambo |
| 2003/0225392 A1 | 12/2003 | McMichael |
| 2003/0236549 A1 | 12/2003 | Bonadio et al. |
| 2004/0015185 A1 | 1/2004 | Ewers et al. |
| 2004/0024363 A1 | 2/2004 | Goldberg |
| 2004/0049100 A1 | 3/2004 | Butler |
| 2004/0073090 A1 | 4/2004 | Butler |
| 2004/0092795 A1 | 5/2004 | Bonadio et al. |
| 2004/0092796 A1 | 5/2004 | Butler et al. |
| 2004/0093018 A1 | 5/2004 | Johnson |
| 2004/0097793 A1 | 5/2004 | Butler et al. |
| 2004/0106942 A1 | 6/2004 | Taylor et al. |
| 2004/0143158 A1 | 7/2004 | Hart et al. |
| 2004/0154624 A1 | 8/2004 | Bonadio et al. |
| 2004/0215063 A1 | 10/2004 | Bonadio et al. |
| 2004/0230161 A1 | 11/2004 | Zeiner |
| 2004/0249248 A1 | 12/2004 | Bonadio et al. |
| 2005/0020884 A1 | 1/2005 | Heart et al. |
| 2005/0033246 A1 | 2/2005 | Ahlberg |
| 2005/0059865 A1 | 3/2005 | Kahle et al. |
| 2005/0065543 A1 | 3/2005 | Kahle et al. |
| 2005/0090713 A1 | 4/2005 | Gozales |
| 2005/0090716 A1 | 4/2005 | Bonadio et al. |
| 2005/0090717 A1 | 4/2005 | Bonadio et al. |
| 2005/0131349 A1 | 6/2005 | Albrecht |
| 2005/0137609 A1 | 6/2005 | Guiraudon |
| 2005/0148823 A1 | 7/2005 | Vaugh et al. |
| 2005/0155611 A1 | 7/2005 | Vaugh et al. |
| 2005/0159647 A1 | 7/2005 | Hart et al. |
| 2005/0192483 A1 | 9/2005 | Bonadio et al. |
| 2005/0192598 A1 | 9/2005 | Johnson |
| 2005/0197537 A1 | 9/2005 | Bonadio et al. |
| 2005/0203346 A1 | 9/2005 | Bonadio et al. |
| 2005/0209510 A1 | 9/2005 | Bonadio et al. |
| 2005/0240082 A1 | 10/2005 | Bonadio et al. |
| 2005/0241647 A1 | 11/2005 | Nguyen |
| 2005/0277946 A1 | 12/2005 | Greenhalgh |
| 2005/0288558 A1 | 12/2005 | Ewers |
| 2005/0288634 A1 | 12/2005 | O'Herron |
| 2006/0020164 A1 | 1/2006 | Butler et al. |
| 2006/0020241 A1 | 1/2006 | Piskun et al. |
| 2006/0041270 A1 | 2/2006 | Lenker et al. |
| 2006/0047284 A1 | 3/2006 | Gresham |
| 2006/0106402 A1 | 5/2006 | McLucas |
| 2006/0149306 A1 | 7/2006 | Hart et al. |
| 2006/0161050 A1 | 7/2006 | Butler et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0258899 A1 | 11/2006 | Gill et al. |
| 2006/0264706 A1 | 11/2006 | Piskun |
| 2007/0004968 A1 | 1/2007 | Bonadio et al. |
| 2007/0049966 A1 | 3/2007 | Bonadio et al. |
| 2007/0093695 A1 | 4/2007 | Bonadio et al. |
| 2007/0118175 A1 | 5/2007 | Butler et al. |
| 2007/0185387 A1 | 8/2007 | Albrecht et al. |
| 2007/0203398 A1 | 8/2007 | Bonadio et al. |
| 2007/0255219 A1 | 11/2007 | Vaugh et al. |
| 2007/0299387 A1 | 12/2007 | Williams et al. |
| 2008/0027476 A1 | 1/2008 | Piskun |
| 2008/0097162 A1 | 4/2008 | Bonadio et al. |
| 2008/0097163 A1 | 4/2008 | Butler et al. |
| 2008/0255519 A1 | 10/2008 | Piskun et al. |
| 2008/0281161 A1 | 11/2008 | Albrecht et al. |
| 2008/0281162 A1 | 11/2008 | Albrecht et al. |
| 2009/0012477 A1 | 1/2009 | Norton et al. |
| 2009/0036745 A1 | 2/2009 | Bonadio et al. |
| 2009/0069837 A1 | 3/2009 | Bonadio et al. |
| 2009/0149714 A1 | 6/2009 | Bonadio |
| 2009/0187079 A1 | 7/2009 | Albrecht et al. |
| 2009/0292176 A1 | 11/2009 | Bonadio et al. |
| 2009/0326330 A1 | 12/2009 | Bonadio et al. |
| 2010/0063362 A1 | 3/2010 | Bonadio et al. |
| 2010/0063364 A1 | 3/2010 | Bonadio et al. |
| 2010/0204548 A1 | 8/2010 | Bonadio et al. |

FOREIGN PATENT DOCUMENTS

| | | |
|---|---|---|
| DE | 296 00 939 | 6/1998 |
| EP | 0113520 | 7/1984 |
| EP | 0142262 | 5/1985 |
| EP | 0537768 | 4/1993 |
| EP | 0950376 | 10/1999 |
| EP | 1118657 | 7/2001 |
| FR | 1456623 | 9/1966 |
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |
| GB | 1496696 | 12/1977 |
| GB | 2071502 | 9/1981 |
| GB | 2255019 | 10/1992 |
| GB | 2275420 | 8/1994 |
| JP | 10-108868 | 4/1998 |
| JP | 11-290327 | 10/1999 |
| JP | 2001-61850 | 3/2001 |
| JP | 2002-28163 | 1/2002 |
| JP | 2004-195037 | 7/2004 |
| SU | 1342485 | 1/1997 |
| WO | WO 86/06272 | 11/1986 |
| WO | WO 92/11880 | 7/1992 |
| WO | WO 92/21292 | 12/1992 |
| WO | WO 93/05740 | 4/1993 |
| WO | WO 95/05207 | 2/1995 |
| WO | WO 95/07056 | 3/1995 |
| WO | WO 95/22289 | 8/1995 |
| WO | WO 95/24864 | 9/1995 |
| WO | WO 95/27445 | 10/1995 |
| WO | WO 95/27468 | 10/1995 |
| WO | WO 96/36283 | 11/1996 |
| WO | WO 97/32514 | 9/1997 |
| WO | WO 97/32515 | 9/1997 |
| WO | WO 98/35614 | 8/1998 |
| WO | WO 98/48724 | 11/1998 |
| WO | WO 99/03416 | 1/1999 |
| WO | WO 99/25268 | 5/1999 |
| WO | WO 99/29250 | 6/1999 |
| WO | WO 00/32116 | 6/2000 |
| WO | WO 00/32117 | 6/2000 |
| WO | WO 00/32119 | 6/2000 |
| WO | WO 00/32120 | 6/2000 |
| WO | WO 00/35356 | 6/2000 |
| WO | WO 00/54675 | 9/2000 |
| WO | WO 00/54676 | 9/2000 |
| WO | WO 00/54677 | 9/2000 |
| WO | WO 01/08563 | 2/2001 |
| WO | WO 01/08581 | 2/2001 |
| WO | WO 01/26558 | 4/2001 |

(56) References Cited

FOREIGN PATENT DOCUMENTS

| | | |
|---|---|---|
| WO | WO 01/91652 | 12/2001 |
| WO | WO 02/17800 A2 | 3/2002 |
| WO | WO 02/34108 A2 | 5/2002 |
| WO | WO 03/026512 A1 | 4/2003 |
| WO | WO 03/034908 A3 | 5/2003 |
| WO | WO 03/061480 A1 | 7/2003 |
| WO | WO 03/103548 A1 | 12/2003 |
| WO | WO 2004/026153 A1 | 4/2004 |
| WO | WO 2004/030547 A1 | 4/2004 |
| WO | WO 2005/009257 A2 | 2/2005 |
| WO | WO 2005/034766 A2 | 4/2005 |
| WO | WO 2005/089661 | 9/2005 |
| WO | WO 2006/040748 A1 | 4/2006 |
| WO | WO 2006/059318 | 8/2006 |
| WO | WO 2008/121294 A1 | 10/2008 |
| WO | WO 2009/035663 A2 | 3/2009 |

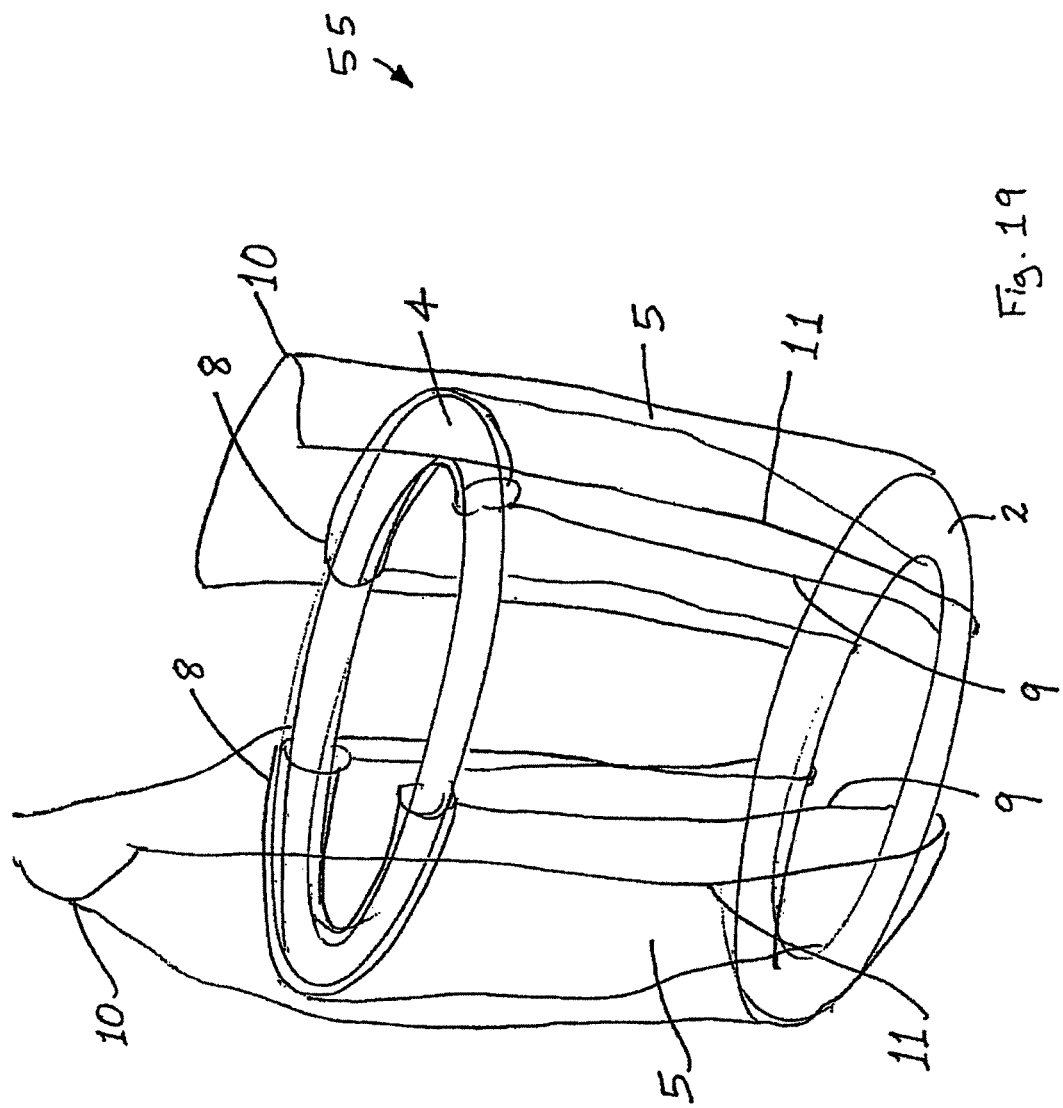

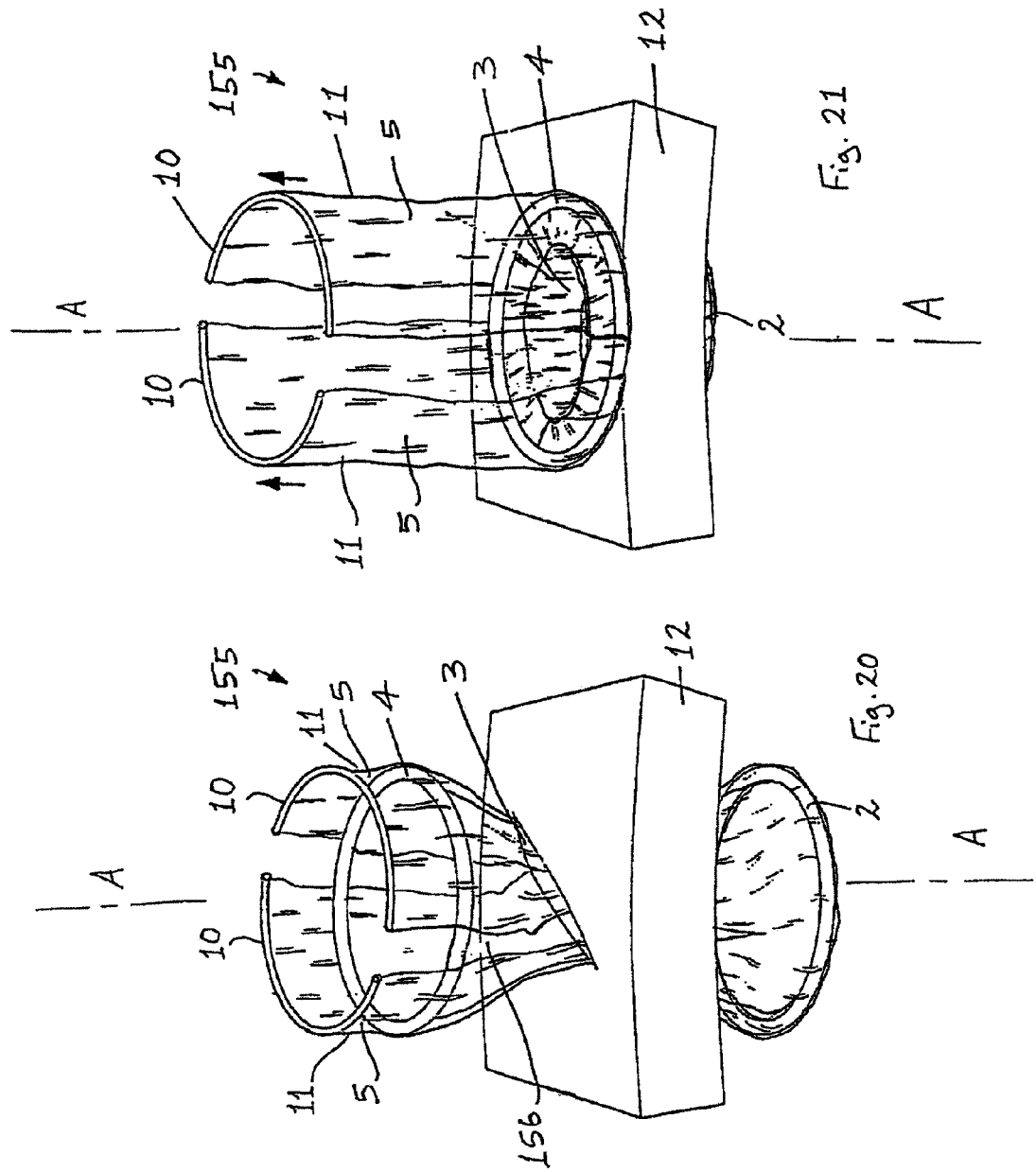

WOUND RETRACTOR DEVICE

This is a continuation of application Ser. No. 11/086,661, filed Mar. 23, 2005, now U.S. Pat. No. 7,537,564, which is a continuation-in-part of application Ser. No. 10/995,117, filed Nov. 24, 2004, now U.S. Pat. No. 7,300,399, which is a continuation of application Ser. No. 10/133,979, filed Apr. 29, 2002, now U.S. Pat. No. 6,846,287, which is a continuation of application Ser. No. 09/801,826, filed Mar. 9, 2001, now abandoned, which is a continuation of PCT International Application No. PCT/IE99/00122, filed Dec. 1, 1999. Application Ser. No. 11/086,661 claims the benefit of U.S. Provisional Application No. 60/555,398, filed on Mar. 23, 2004. The contents of all of the above-listed applications are incorporated herein by reference.

INTRODUCTION

This invention relates to a wound retractor device, and to a method of retracting a wound opening.

STATEMENTS OF INVENTION

According to the invention there is provided a wound retractor device comprising:
- a distal member for insertion into a wound opening;
- a proximal member for location externally of the wound opening; and
- a connecting member extending at least between the distal member and the proximal member;
- at least part of the connecting member being movable relative to the proximal member to shorten the length of the connecting member located between the distal member and the proximal member and thereby retract laterally the sides of the wound opening.

In one embodiment of the invention the connecting member comprises at least one strap member. The connecting member may comprise two or more strap members. In one case a first strap member is separate from a second strap member. In another case a first strap member is attached to a second strap member.

The connecting member may comprise a sleeve member. The sleeve member may provide the means of attachment of the first strap member to the second strap member. In one case the first strap member extends from the sleeve member in a first direction, and the second strap member extends from the sleeve member in the first direction. The sum of the circumferential dimensions of the strap members may be substantially equal to the circumferential dimension of the sleeve member. The strap member may be attached to an end of the sleeve member. In one case the first strap member is attached to a first end of the sleeve member, and the second strap member is attached to the first end of the sleeve member.

In one case the connecting member is axially movable relative to the proximal member.

At least part of the connecting member may be movable relative to the proximal member in a lateral direction. In one case at least part of the connecting member is movable relative to the proximal member in a direction substantially perpendicular to a longitudinal axis of a wound opening. In another case at least part of the connecting member is movable relative to the proximal member in a direction substantially parallel to a longitudinal axis of a wound opening.

At least part of the connecting member may be slidably movable relative to the proximal member.

In one embodiment of the invention the device comprises a guide to guide movement of the connecting member relative to the proximal member. The guide may comprise a passageway through which the connecting member is extendable. The passageway may be provided by a slot in the proximal member. A longitudinal axis of the passageway may be substantially perpendicular to a longitudinal axis of a wound opening. A longitudinal axis of the passageway may be substantially parallel to a longitudinal axis of a wound opening.

In one case the connecting member is movable relative to the distal member. The device may comprise a guide to guide movement of the connecting member relative to the distal member. The guide may comprise a passageway through which the connecting member is extendable. In one case the passageway is provided by a slot in the distal member. A longitudinal axis of the passageway may be substantially perpendicular to a longitudinal axis of a wound opening. A longitudinal axis of the passageway may be substantially parallel to a longitudinal axis of a wound opening.

In one embodiment the connecting member extends between the distal member and the proximal member in a double layer. The connecting member may be looped around at least part of the distal member. In one case a first end of the connecting member is fixed relative to the proximal member. A second end of the connecting member may be movable relative to the proximal member. In one case the connecting member extends from the first end distally to the distal member in a first layer, and extends from the distal member proximally to the second end in a second layer, the second layer being radially outwardly of the first layer. In another case the connecting member extends from the first end distally to the distal member in a first layer, and extends from the distal member proximally to the second end in a second layer, the second layer being radially inwardly of the first layer.

In one case the device is configured to self-lock the connecting member in position relative to the proximal member.

In a further embodiment the connecting member is fixed relative to the distal member.

The connecting member may extend between the distal member and the proximal member in a single layer.

In one case at least part of the connecting member is grippable to move at least part of the connecting member relative to the proximal member. The grippable part of the connecting member may be configured to the located externally of a wound opening.

In a further embodiment the device comprises a lock to releasably lock the connecting member in position relative to the proximal member. The lock may comprise a male protrusion for co-operating engagement with a female recess.

In one case the proximal member comprises the male protrusion, and the connecting member comprises the female recess. The lock may comprise a plurality of female recesses.

In another case the lock comprises an engagement member releasably fixable to the connecting member to engage against the proximal member. The engagement member may comprise a clamp.

In another embodiment the device comprises a protector to protect a retracted wound opening. The protector may comprise a sleeve member to line a retracted wound opening. The sleeve member may be mounted to the distal member. In one case a first end of the sleeve member is fixed to the distal member and a second end of the sleeve member is configured for location externally of a wound opening.

The proximal member may comprise a ring. The distal member may comprise a ring. The ring may be substantially circular. The ring may be substantially square-shaped.

In one embodiment the connecting member comprises a plurality of strap members spaced around the circumference of the proximal member and/or the distal member.

In another aspect of the invention there is provided a method of retracting a wound opening, the method comprising the steps of:
 providing a wound retractor device comprising a distal member, a proximal member, and a connecting member extending at least between the distal member and the proximal member;
 inserting the distal member into the wound opening, and locating the proximal member externally of the wound opening; and
 moving at least part of the connecting member relative to the proximal member to shorten the length of the connecting member located between the distal member and the proximal member and thereby retract laterally the sides of the wound opening.

In one case at least part of the connecting member is moved relative to the proximal member in a lateral direction. At least part of the connecting member may be moved relative to the proximal member in a direction substantially perpendicular to a longitudinal axis of the wound opening.

In another case at least part of the connecting member is moved relative to the proximal member in a direction substantially parallel to a longitudinal axis of the wound opening. At least part of the connecting member may be slidably moved relative to the proximal member.

The method may comprise the steps of gripping at least part of the connecting member and exerting a force on the connecting member to move at least part of the connecting member relative to the proximal member. In one case the method comprises the step of releasing the connecting member after lateral retraction of the sides of the wound opening.

In one embodiment the method comprises the step of guiding movement of the connecting member relative to the proximal member.

In another case the method comprises the step of moving the connecting member relative to the distal member. The method may comprise the step of guiding movement of the connecting member relative the distal member.

In one case the connecting member is locked in position relative to the proximal member after lateral retraction of the sides of the wound opening. In one case the wound retractor device self-locks the connecting member in position relative to the proximal member.

In another case the method comprises the step of releasably locking the connecting member in position relative to the proximal member. The connecting member may be releasably locked in position relative to the proximal member by engaging a male protrusion with a female recess. The connecting member may be releasably locked in position relative to the proximal member by fixing an engagement member to the connecting member, and engaging the engagement member against the proximal member.

The method may comprise the step of protecting the retracted wound opening. The method may comprise the step of locating a protector between the connecting member and the sides of the wound opening. In one case step of locating the protector between the connecting member and the sides of the wound opening is performed after the distal member is inserted into the wound opening. In one case the protector is inserted into the wound opening with the distal member. The protector may be retrieved from within the wound opening to locate the protector between the connecting member and the sides of the wound opening.

BRIEF DESCRIPTION OF THE DRAWINGS

The invention will be more clearly understood from the following description of some embodiments thereof, given by way of example only, with reference to the accompanying drawings, in which:

FIG. 19 is a perspective view of another wound retractor device according to the invention;
FIGS. 20 and 21 are perspective views of another wound retractor device according to the invention, in use.

DETAILED DESCRIPTION

Figure 1:
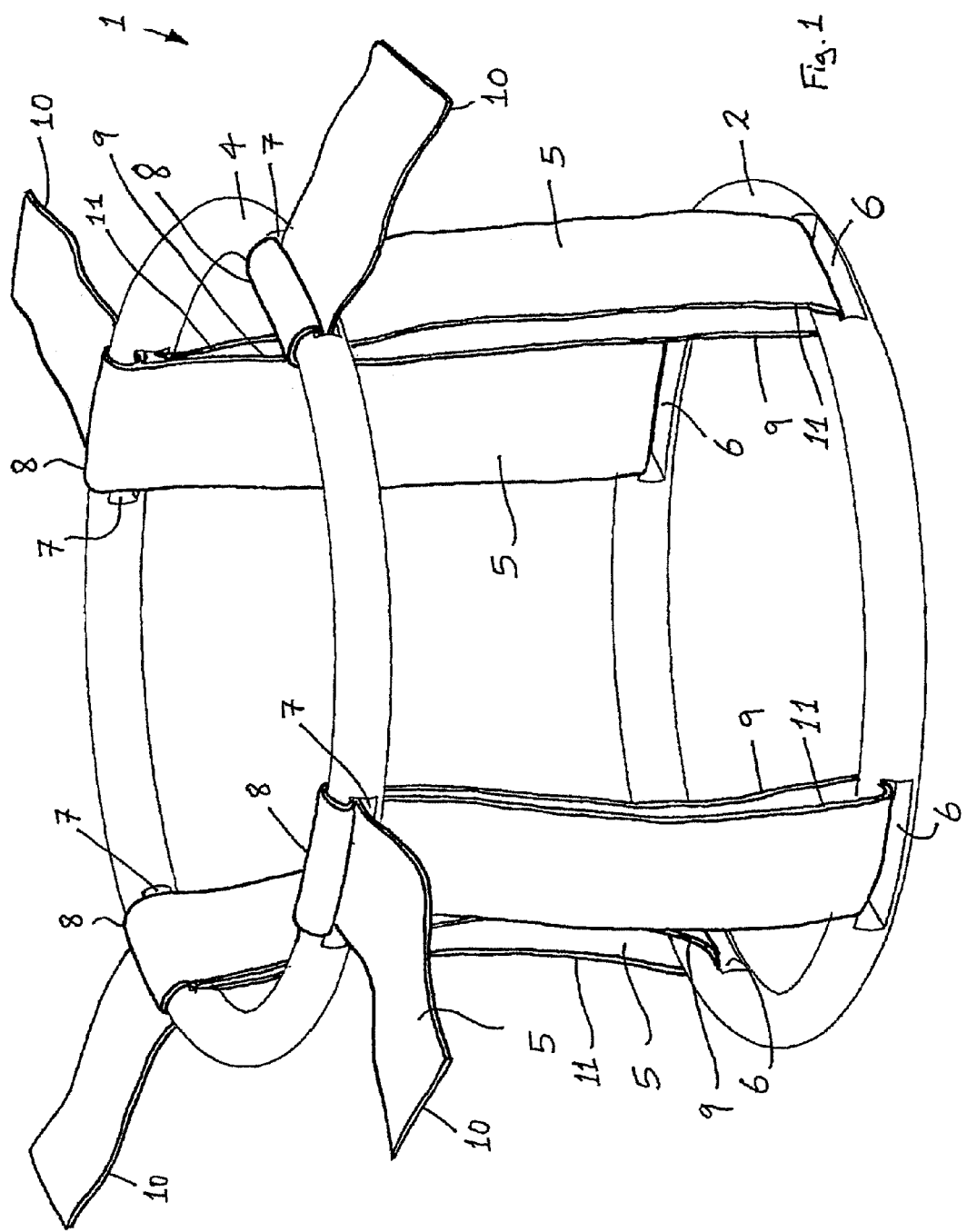
FIG. 1 is a perspective view of a wound retractor device according to the invention.
Figure 2:
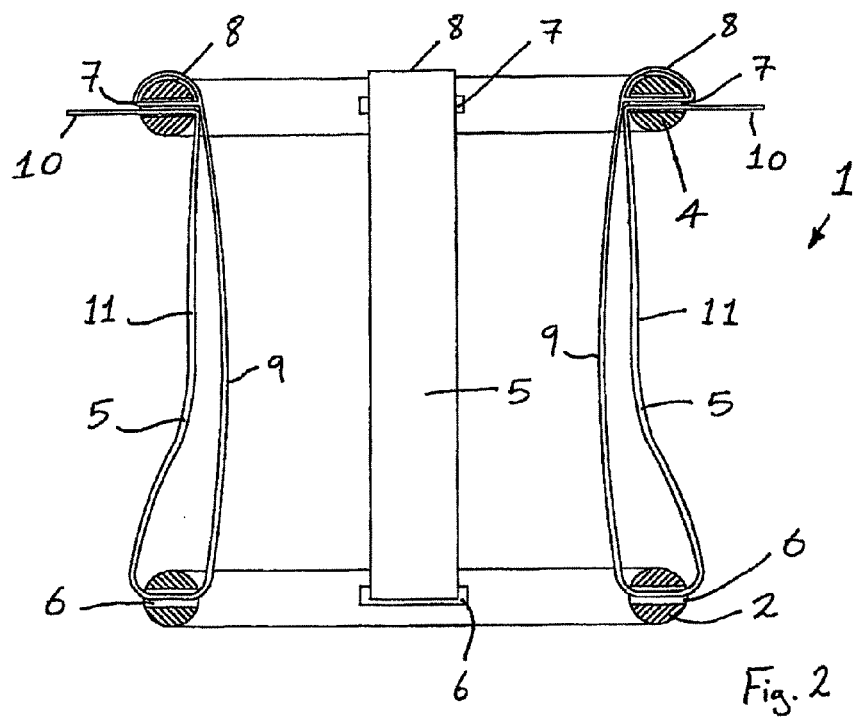
FIG. 2 is a cross-sectional, side view of the device of FIG. 1.
Figure 3:
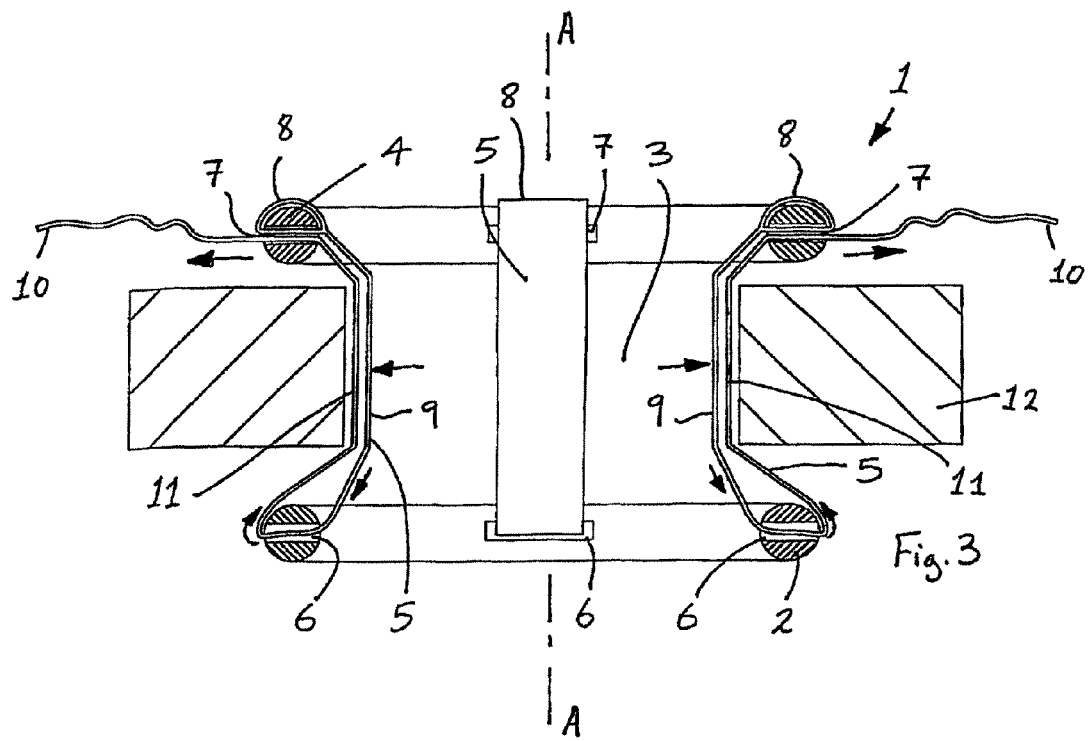
FIG. 3 is a cross-sectional, side view of the device of FIG. 1, in use.

Referring to the drawings, and initially to FIGS. 1 to 3 thereof, there is illustrated a wound retractor device 1 according to the invention. The device 1 comprises a distal ring member 2 for insertion into a wound opening 3, a proximal ring member 4 for location externally of the wound opening 3, and a connecting member extending between the proximal ring member 4 and the distal ring member 2. In this case the connecting member is provided in the form of four separate strap members 5 which are axially movable relative to the distal ring member 2 and relative to the proximal ring member 4. As illustrated in FIG. 1, the distal ring member 2 and the proximal ring member 4 are substantially circular.

The distal ring member 2 comprises four slots 6, with each strap member 5 positioned extending though a slot 6 (FIG. 1). Each strap member 5 is movable relative to the distal member 2 by sliding of the strap member 5 through the slot 6. The slots 6 thus act as passageways through which the strap members 5 may extend, and in this manner the slots 6 guide movement of the strap members 5 relative to the distal ring member 2. As illustrated in FIGS. 2 and 3, the longitudinal axis of each slot 6 is substantially perpendicular to a longitudinal axis A-A of the wound opening 3.

The proximal ring member 4 also comprises four slots 7 with each strap member 5 positioned extending through a slot 7 (FIG. 1). Each strap member 5 is movable relative to the proximal member 4 by sliding of the strap member 5 through the slot 7. The slots 7 thus act as passageways through which the strap members 5 may extend, and in this manner the slots 7 guide movement of the strap members 5 relative to the proximal ring member 4. As illustrated in FIGS. 2 and 3, the longitudinal axis of each slot 7 is substantially perpendicular to the longitudinal axis A-A of the wound opening 3.

A first end 8 of each strap member 5 is fixedly attached to the proximal ring member 4, with each strap member 5 extending between the distal ring member 2 and proximal ring member 4 in a double layer. In particular, each strap member 5 extends from the first end 8 fixed to the proximal ring member 4 distally towards the distal ring member 2 in a first layer 9. At the distal ring member 2, each strap member 5 is looped through the slot 6. Each strap member 5 then extends from the distal ring member 2 proximally to a second end 10 of the strap member 5 in a second layer 11. As illustrated in FIGS. 2 and 3, the second layer 11 is located radially outwardly of the first layer 9, with the second layer 11 bearing against the sides of the wound opening 3 (FIG. 3).

The four strap members 5 are evenly spaced around the circumference of the distal ring member 2 and around the circumference of the proximal ring member 4. In this manner, an even retracting force is applied to the sides of the wound opening 3.

In use, the distal ring member 2 is inserted into the wound opening 3, and the proximal ring member 4 is located externally of the wound opening 3. The second end 10 of each strap member 5 is then gripped, and a pulling force is exerted on each second end 10 to pull each second end 10 laterally, radially outwardly parallel to the longitudinal axis of the slots 7 away from the proximal ring member 4, as illustrated in FIG. 3. This pulling action causes each strap member 5 to be pulled axially through the slot 6 in the distal ring member 2 in a sliding manner and through the slot 7 in the proximal ring member 4 in a sliding manner, as indicated by the arrows in FIG. 3.

As a result the length of each strap member 5 which is located between the distal ring member 2 and the proximal ring member 4 is shortened, and initially the distal ring member 2 is drawn upwardly towards the proximal ring member 4. When the distal ring member 4 reaches the inner surfaces of the peritoneum 12, further pulling of each strap member 5 will cause shortening of the length of each strap member 5 which is located between the distal ring member 2 and the proximal ring member 4 by retracting laterally the sides of the wound opening 3 (FIG. 3). After lateral retraction of the sides of the wound opening 3, the second end 10 of each strap member 5 may be released.

As the strap members 5 are pulled and the wound opening 3 is retracted, the slots 6 guide movement of the strap members 5 relative to the distal ring member 2, and the slots 7 guide movement of the strap members 5 relative to the proximal ring member 4. In this way, the slots 6, 7 provide the surgeon with enhanced control of the strap members 5.

The wound retractor device 1 is self-locking. Thus, when the pulling force is released, the strap members 5 remain locked in position with the wound opening 3 retracted (FIG. 3).

Figure 4:
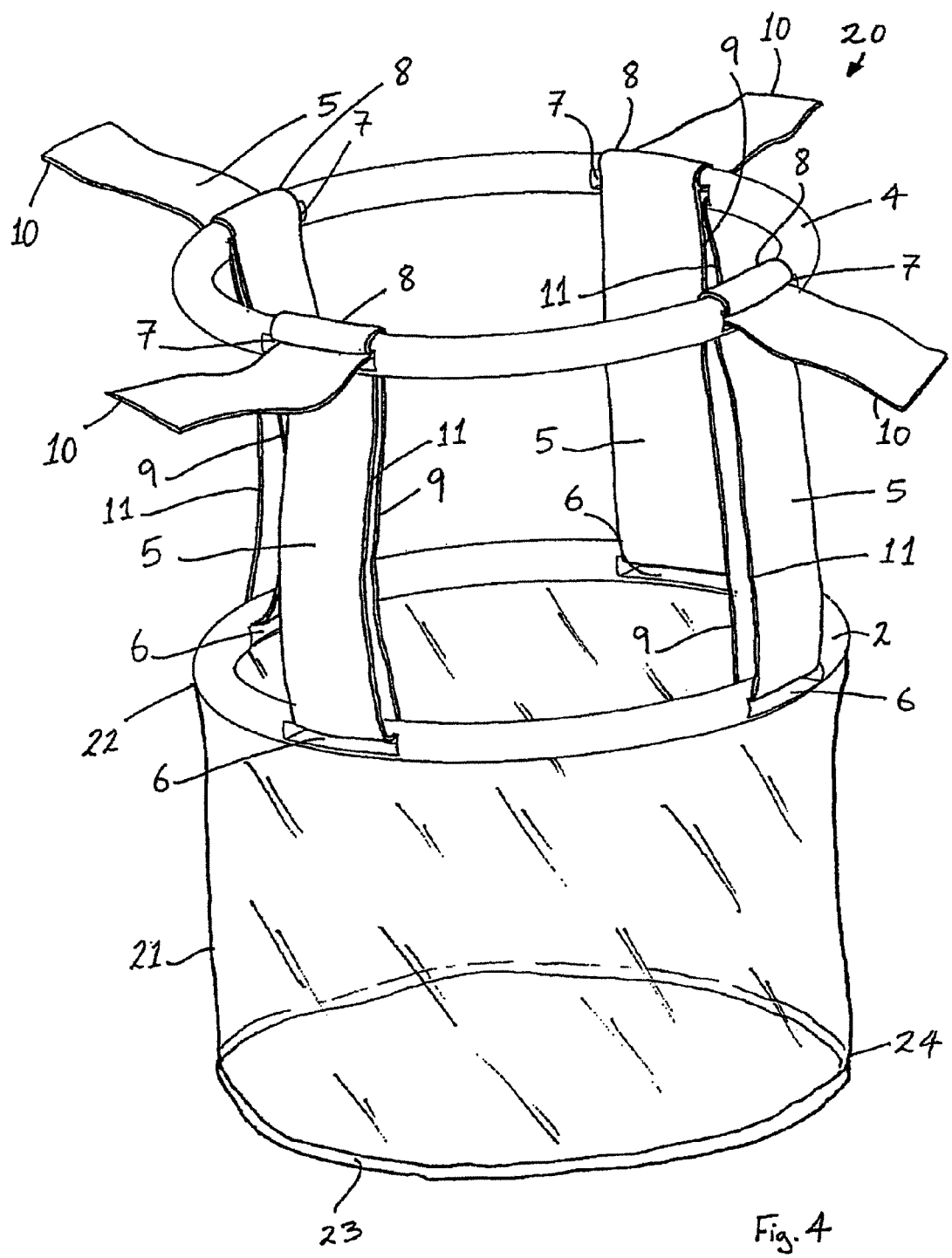
FIGS. 4 to 6 are views similar to FIGS. 1 to 3 of another wound retractor device according to the invention.
Figure 5:
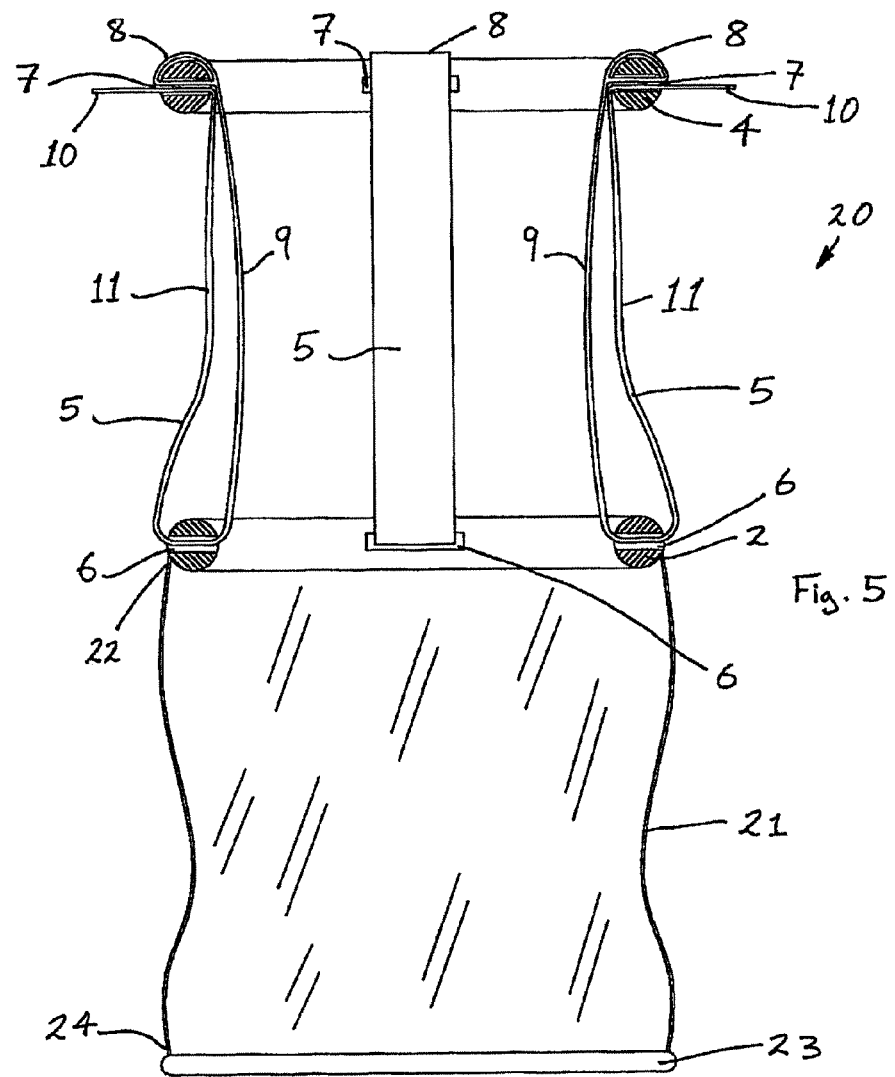
Figure 6:
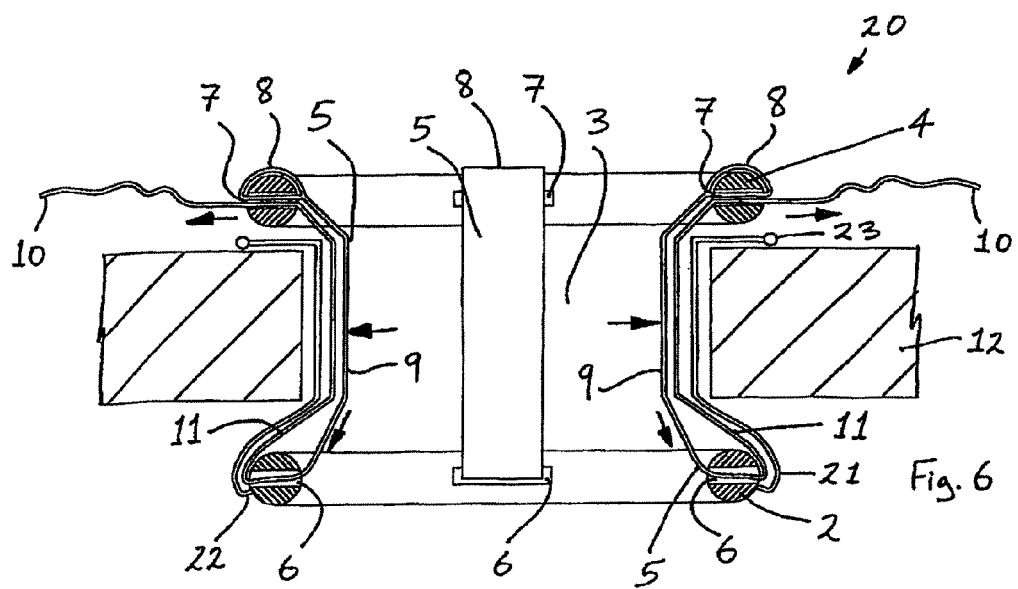

FIGS. 4 to 6 illustrate another wound retractor device 20 according to the invention, which is similar to the device 1 of FIGS. 1 to 3, and similar elements in FIGS. 4 to 6 are assigned the same reference numerals.

In this case, the device 20 comprises a cylindrical film sleeve member 21 for lining the retracted wound opening 3 to protect the retracted wound opening 3. A first end 22 of the sleeve member 21 is mounted to the distal ring member 2 by fixedly attaching the first end 22 to the distal ring member 2. A ring 23 is provided at a second end 24 of the sleeve member 21.

In use, the distal ring member 2 and the sleeve member 21 are together inserted into the wound opening 3. The ring 23 is then gripped and pulled back out of the wound opening 3, and located externally of the wound opening 3 between the proximal ring member 4 and the peritoneum 12, as illustrated in FIG. 6. In this manner, the sleeve member 21 is retrieved from within the wound opening 3 and located between the strap members 5 and the sides of the wound opening 3. Retraction of the wound opening 3 may then be performed as described previously with reference to FIGS. 1 to 3. The sleeve member 21 thus acts to line the retracted wound opening 3 to protect the retracted wound opening 3, as illustrated in FIG. 6.

It will be appreciated that the sleeve member 21 may alternatively be provided disconnected from the distal ring member 2.

Figure 7:
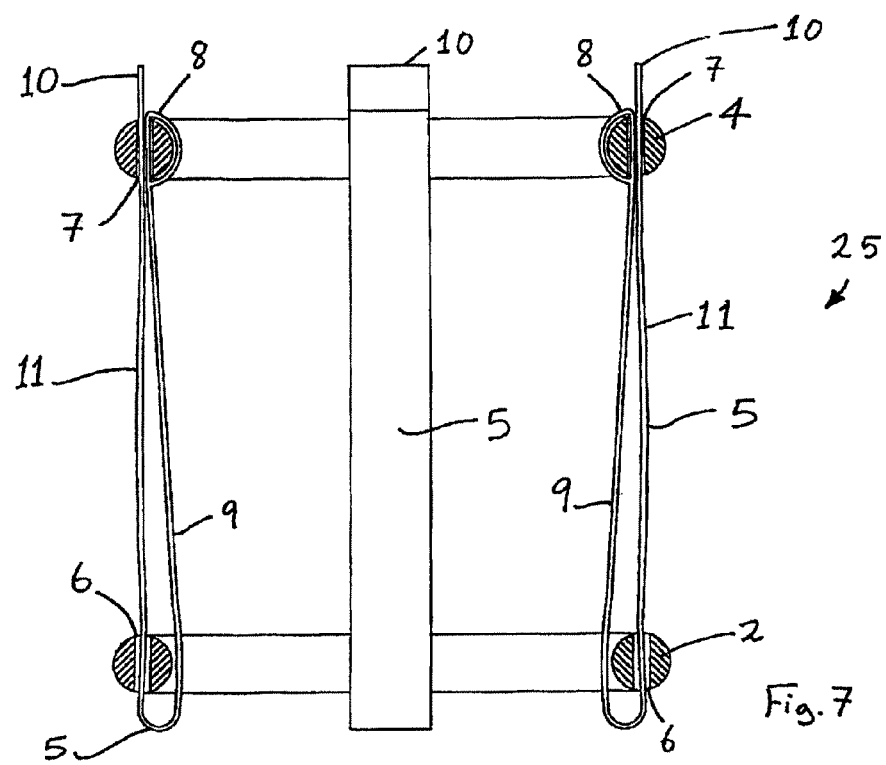
FIGS. 7 and 8 are views similar to FIGS. 2 and 3 of a further wound retractor device according to the invention.
Figure 8:
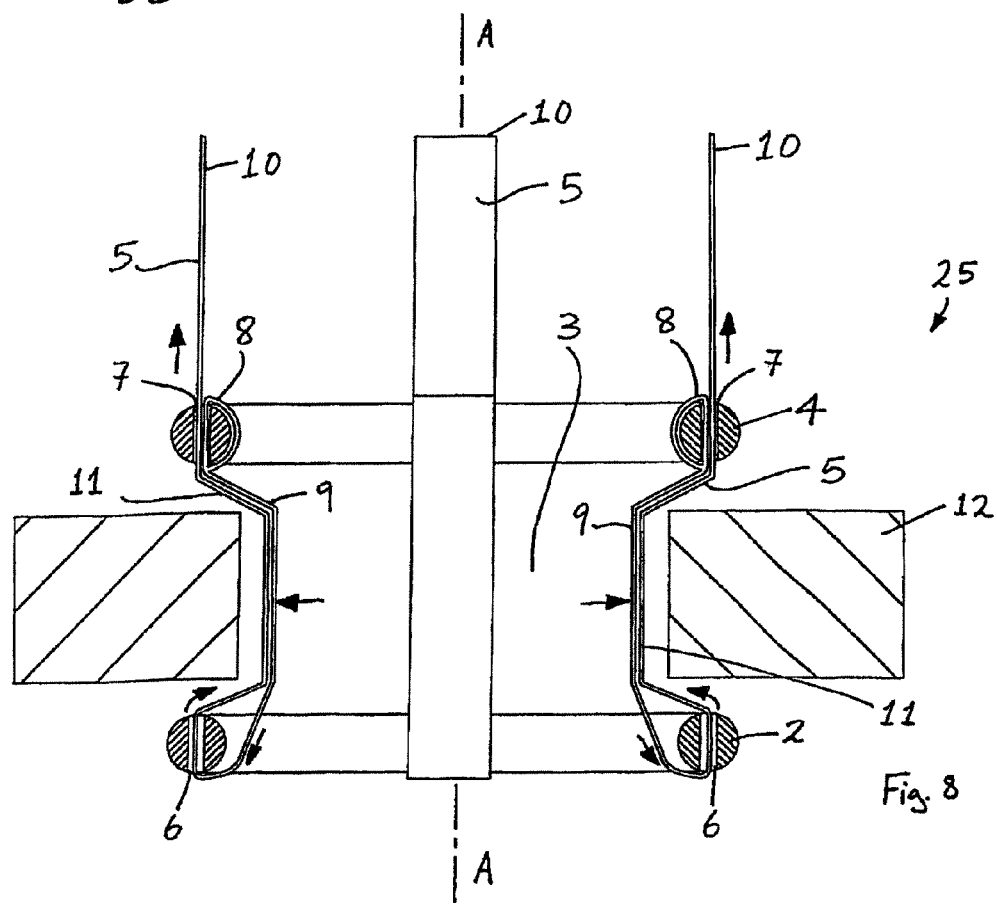

In FIGS. 7 and 8 there is illustrated a further wound retractor device 25 according to the invention, which is similar to the device 1 of FIGS. 1 and 3, and similar elements in FIGS. 7 and 8 are assigned the same reference numerals.

In this case, the longitudinal axis of each slot 6 and the longitudinal axis of each slot 7 are substantially parallel to the longitudinal axis A-A of the wound opening 3. To retract the wound opening 3, the strap members 5 are pulled upwards parallel to the longitudinal axis of the slots 7 away from the proximal ring member 4, as illustrated in FIG. 8.

Figure 9:
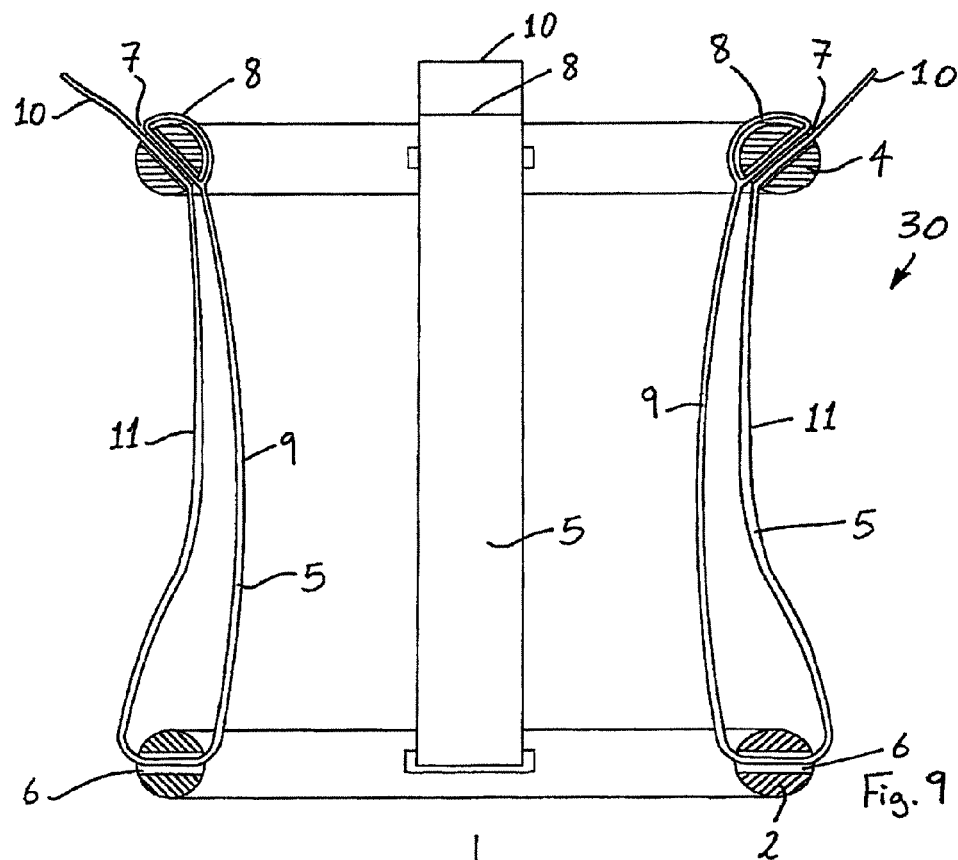
FIGS. 9 and 10 are views similar to FIGS. 2 and 3 of another wound retractor device according to the invention.
Figure 10:
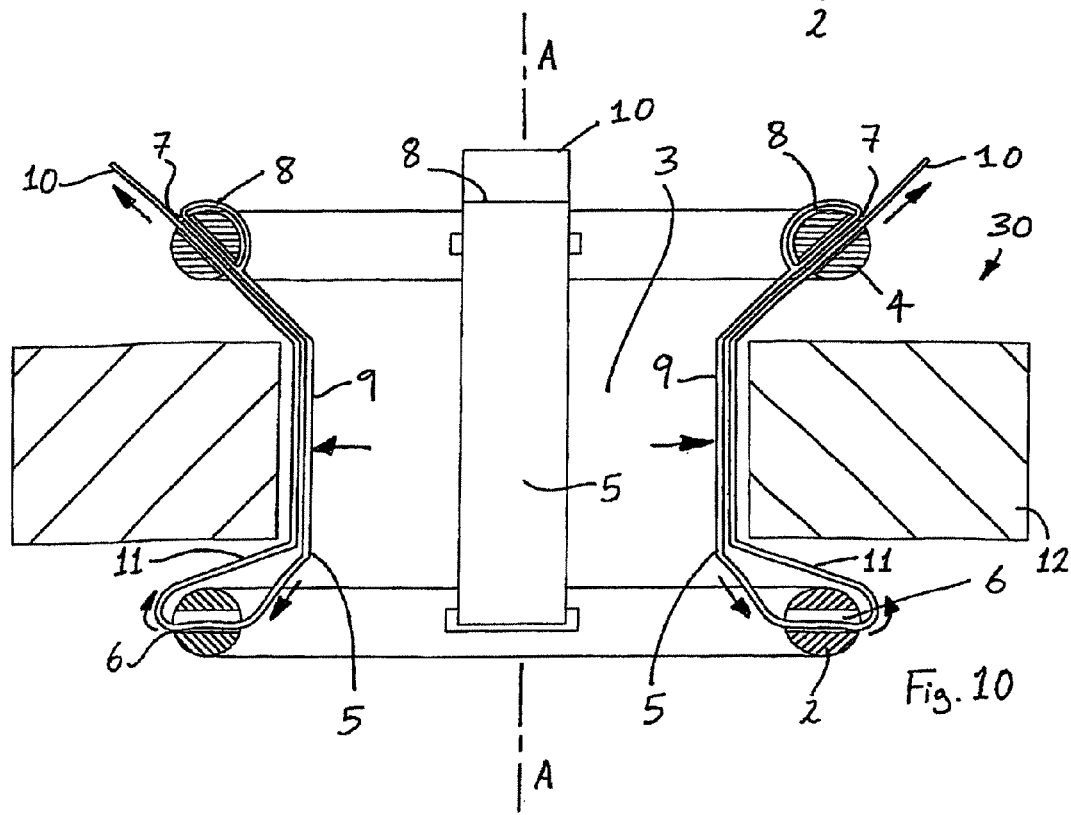

FIGS. 9 and 10 illustrate another wound retractor device 30 according to the invention, which is similar to the device 1 of FIGS. 1 to 3, and similar elements in FIGS. 9 and 10 are assigned the same reference numerals.

In this case, the longitudinal axis of the each slot 7 subtends an acute angle, for example a 45° angle, with the longitudinal axis A-A of the wound opening 3. To retract the wound opening 3, the strap members 5 are pulled upwards parallel to the longitudinal axis of the slots 7 away from the proximal ring member 4, as illustrated in FIG. 10.

It will be appreciated that the longitudinal axis of each slot 6 and/or the longitudinal axis of each slot 7 may be arranged at any suitable angle relative to the longitudinal axis A-A of the wound opening 3.

Figure 11:
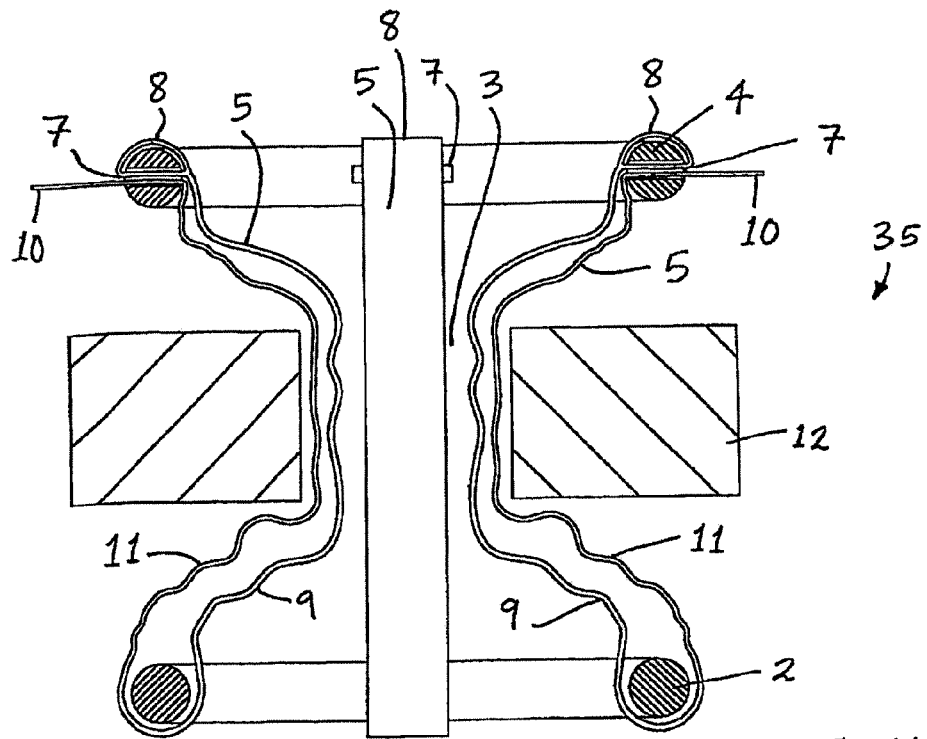
FIGS. 11 and 12 are cross-sectional, side views of a further wound retractor device according to the invention, in use.
Figure 12:
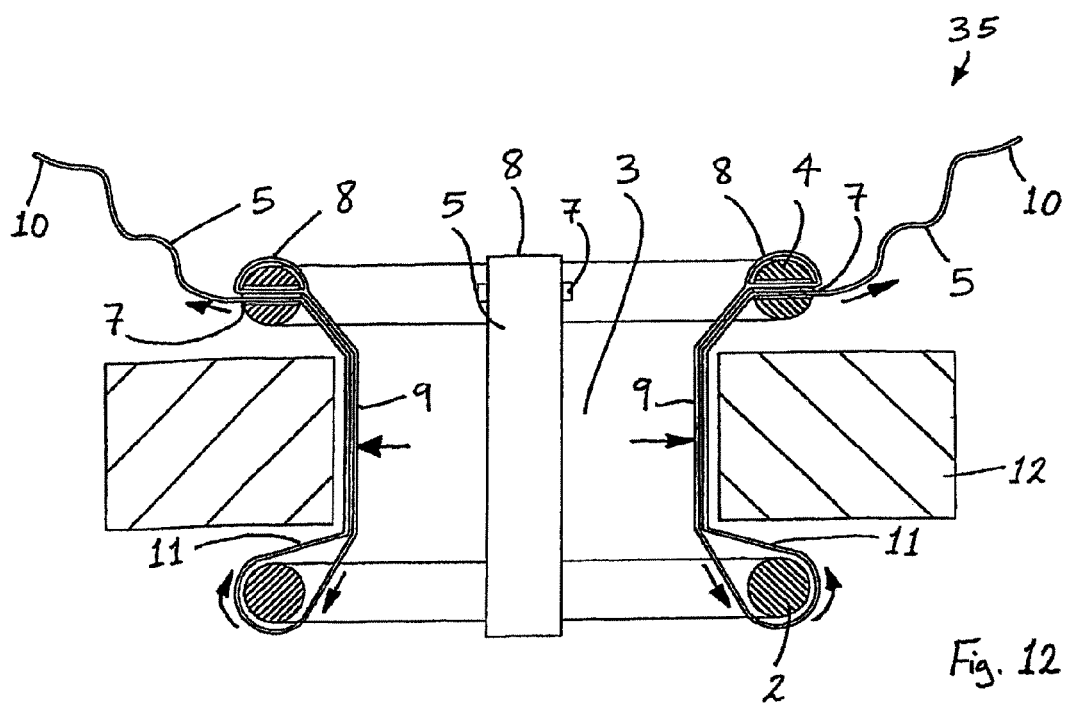

Referring to FIGS. 11 and 12 there is illustrated another wound retractor device 35 according to the invention, which is similar to the device 1 of FIGS. 1 to 3, and similar elements in FIGS. 11 and 12 are assigned the same reference numerals.

In this case, there are no slots provided in the distal ring member 2. Instead each strap member 5 is looped around the entire distal ring member 2. In this manner the distal ring member 2 is associated with the strap members 5.

Figure 13:
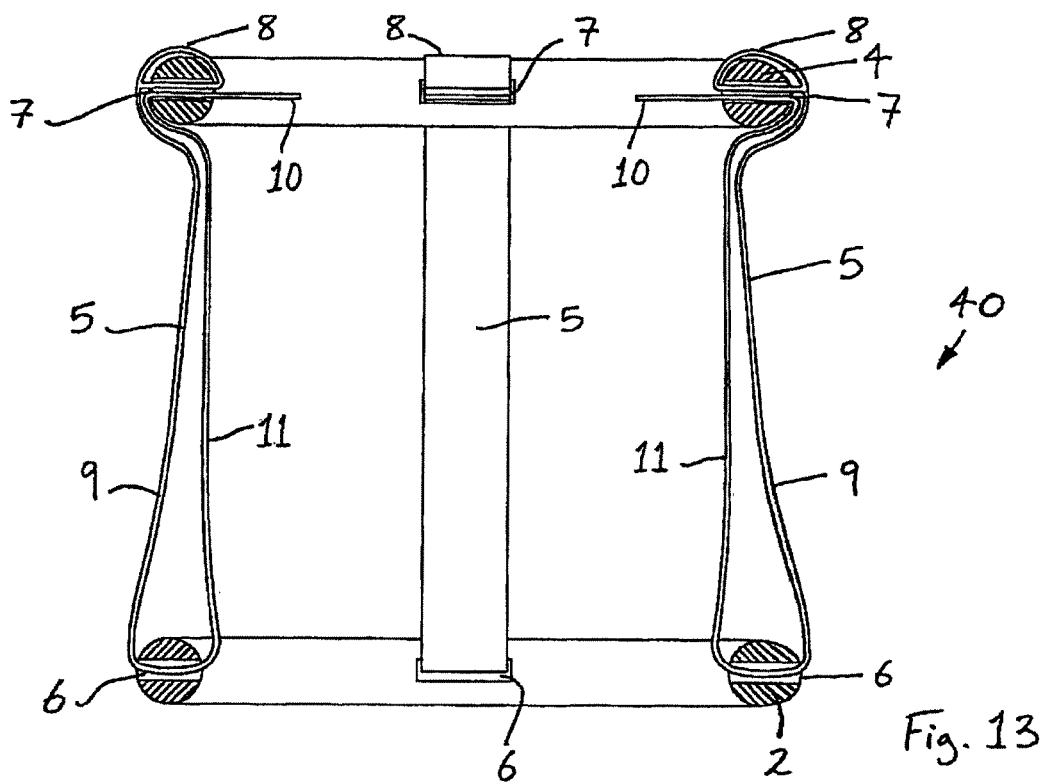
FIGS. 13 and 14 are views similar to FIGS. 2 and 3 of another wound retractor device according to the invention.
Figure 14:
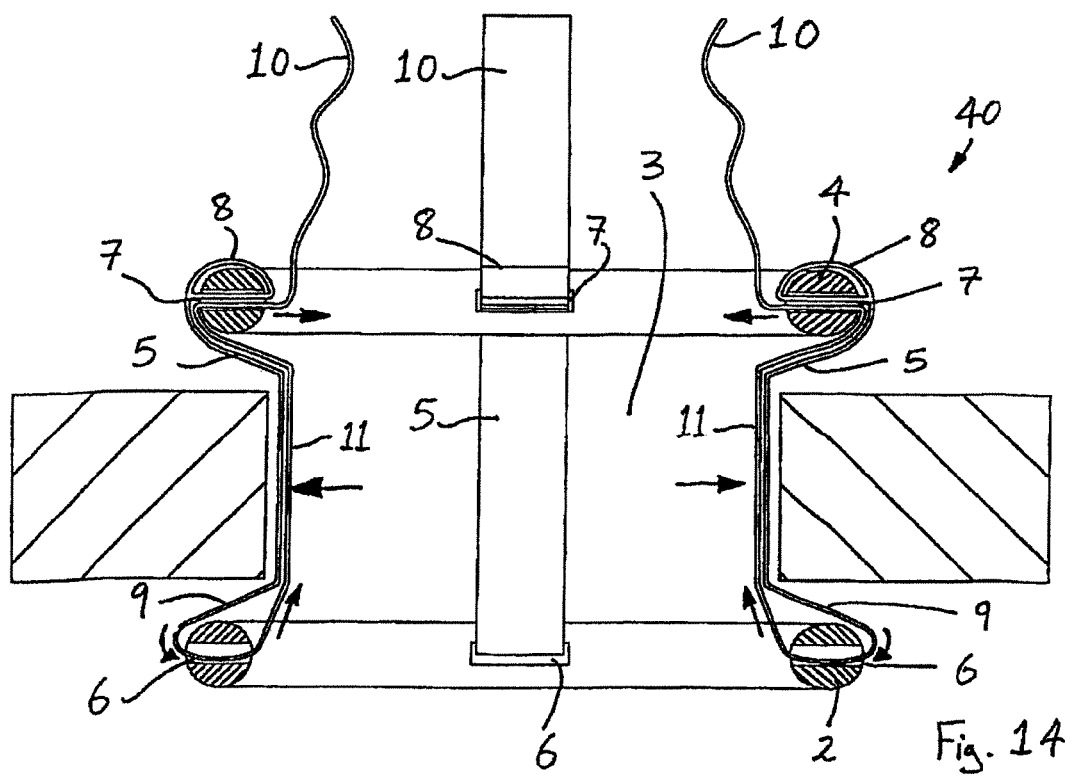

In FIGS. 13 and 14, there is illustrated another wound retractor device 40 according to the invention, which is similar to the device 1 of FIGS. 1 to 3, and similar elements in FIGS. 13 and 14 are assigned the same reference numerals.

In this case, the second layer 11 of each strap member 5 is located radially inwardly of the first layer 9, with the first layer 9 bearing against the sides of the wound opening 3 (FIG. 14). To retract the wound opening 3, the strap members 5 are pulled laterally radially inwardly parallel to the longitudinal axis of the slots 7 away from the proximal ring member 4, as illustrated in FIG. 14.

Figure 15:
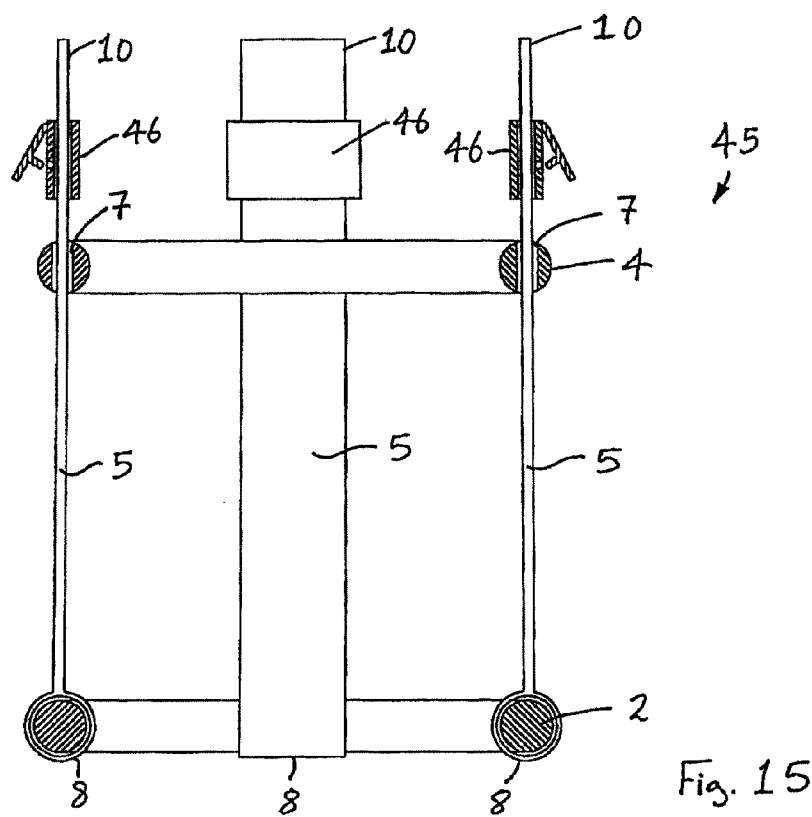
FIGS. 15 and 16 are views similar to FIGS. 2 and 3 of another wound retractor device according to the invention.
Figure 16:
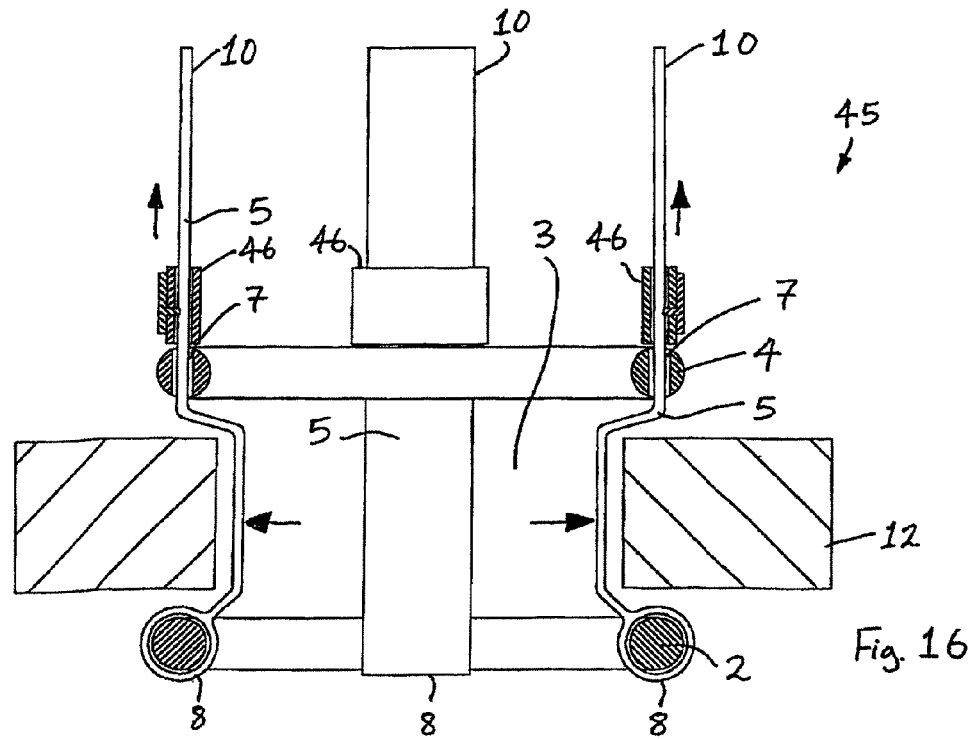

In FIGS. 15 and 16, there is illustrated a further wound retractor device 45 according to the invention.

In this case, there are no slots provided in the distal ring member 2, and the first end 8 of each strap member 5 is fixedly attached to the distal ring member 2. Each strap member 5 extends between the distal ring member 2 and the proximal ring member 4 in a single layer.

In addition, the wound retractor device 45 is not self-locking. Instead the device 45 comprises four clamps 46. Each clamp 46 is releasably fixable to a strap member 5 at a desired location along the strap member 5. When the wound opening 3 has been retracted, each clamp 46 is fixed to a strap member 5 at a location engaging against the proximal ring member 4 (FIG. 16). In this manner, the strap members 5 are releasably locked in position relative to the proximal ring member 4, and the wound opening 3 is thus releasably locked in the retracted configuration.

Figure 17:
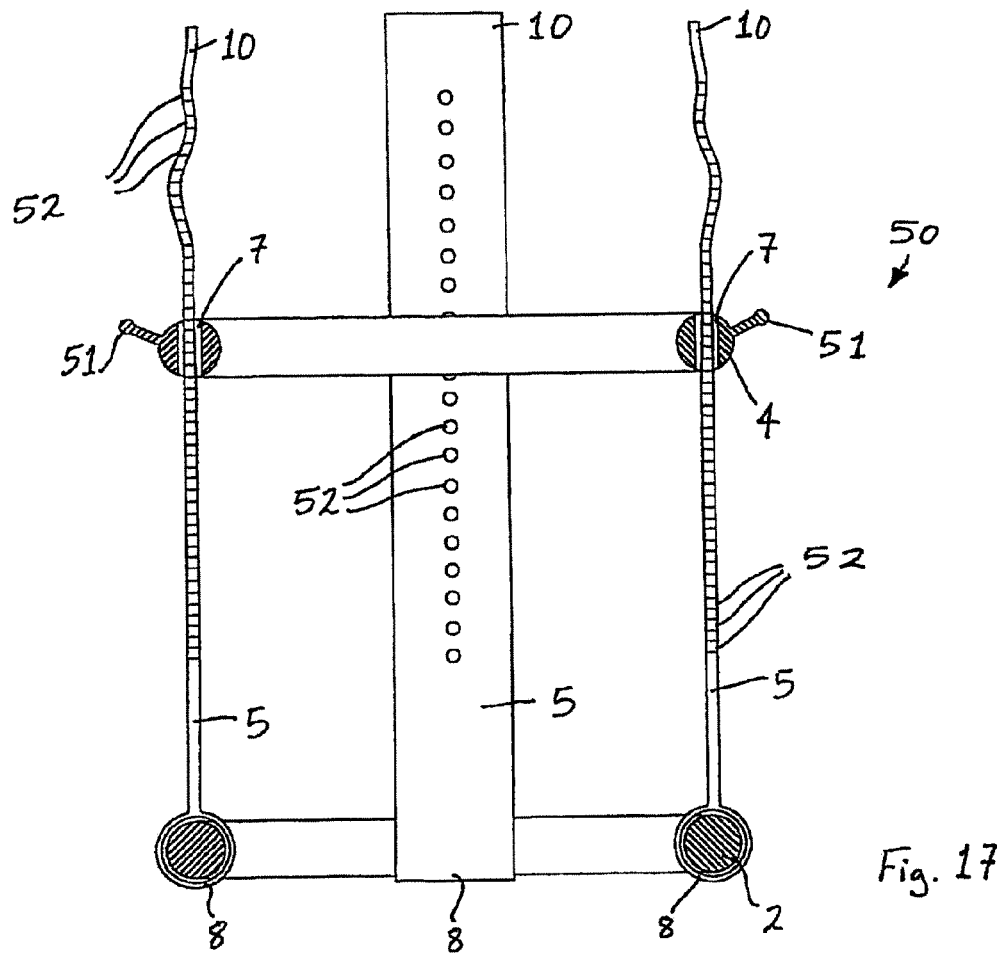
FIGS. 17 and 18 are views similar to FIGS. 2 and 3 of a further wound retractor device according to the invention.
Figure 18:
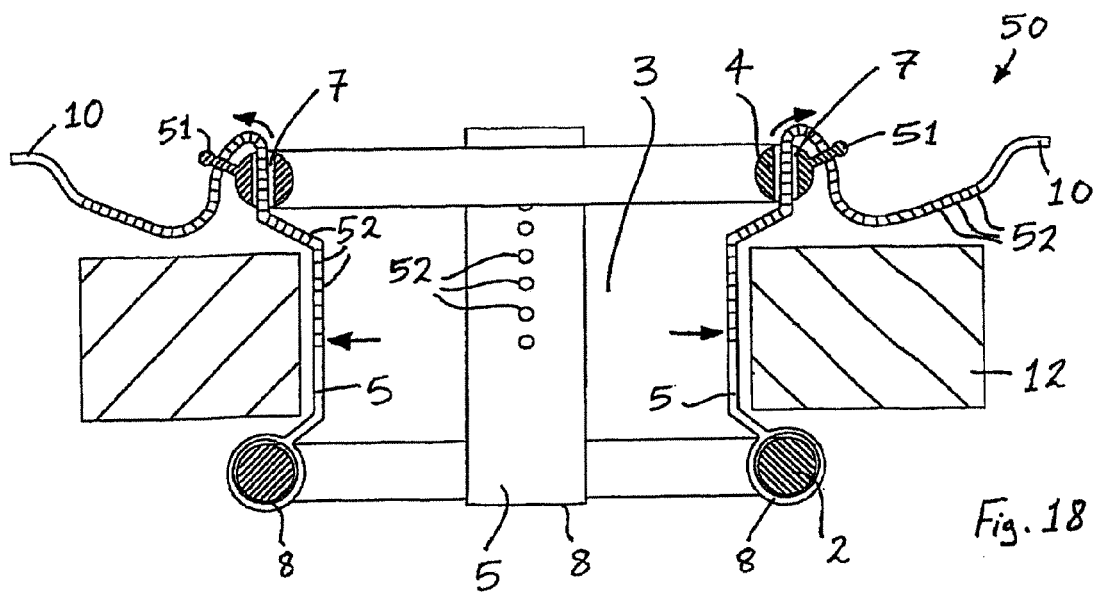

Referring to FIGS. 17 and 18 there is illustrated another wound retractor device 50 according to the invention, which is similar to the device 45 of FIGS. 15 and 16, and similar elements in FIGS. 17 and 18 are assigned the same reference numerals.

In this case, the proximal ring member 4 comprises four male protrusions 51, and each strap member 5 comprises a plurality of female recess openings 52. Each male protrusion 51 is inserted into one of the openings 52 of a strap member 5 for co-operative engagement of the male protrusion 51 with the opening 52 (FIG. 18). In this manner, the strap members 5 are locked in position relative to the proximal ring member 4, and the wound opening 3 is thus locked in the retracted configuration.

FIG. 19 illustrates another wound retractor device 55 according to the invention, which is similar to the device 35 of FIGS. 11 and 12, and similar elements in FIGS. 19 to 21 are assigned the same reference numerals.

In this case, the device 55 comprises two strap members 5, and no slots are provided in the proximal ring member 4.

It will be appreciated that any suitable number of one or more strap members 5 may be provided in the wound retractor device according to the invention to achieve the desired retraction of the wound opening 3.

Figure 21A:
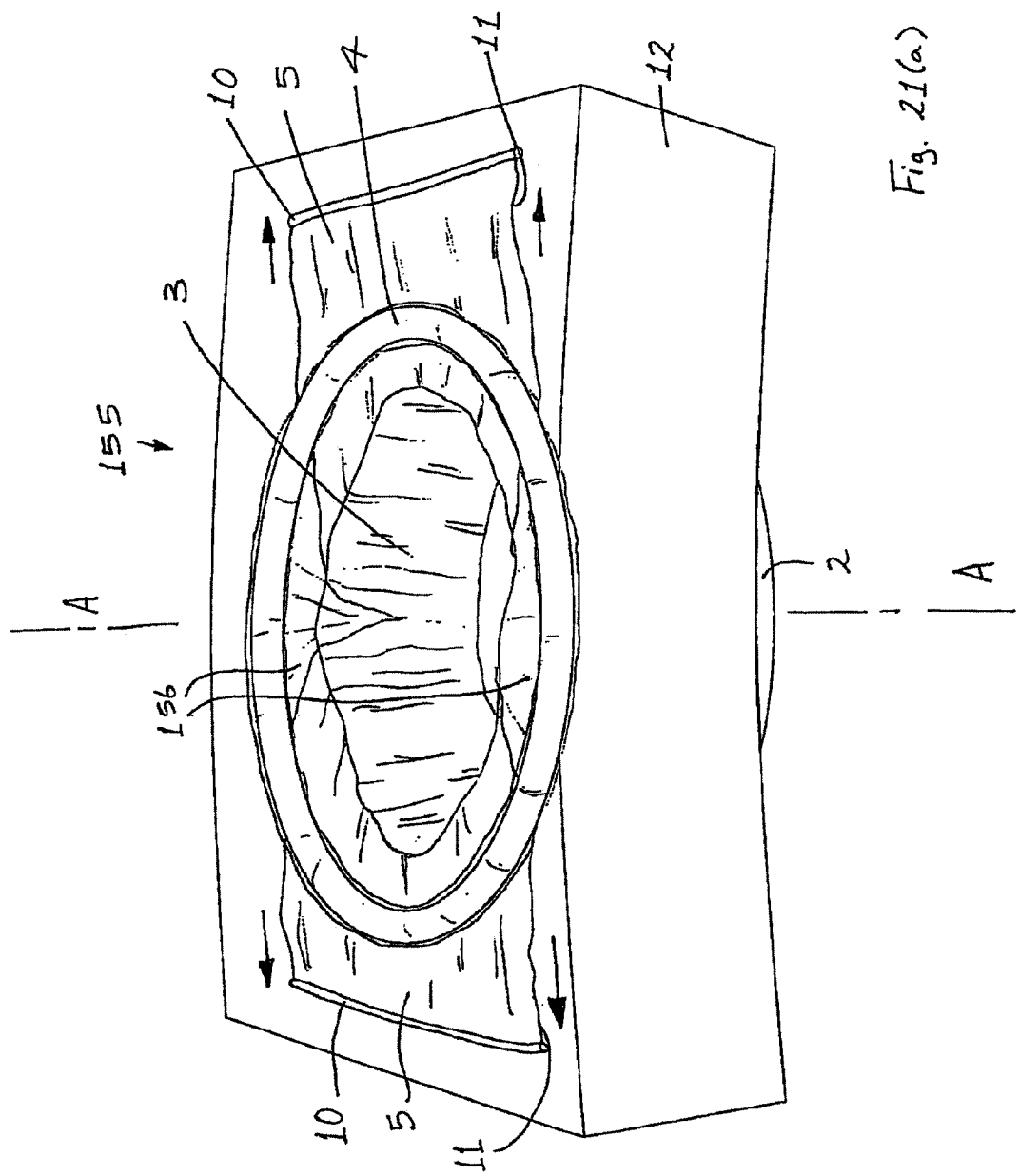
FIG. 21(a) is another perspective view of the device of FIG. 20, in use.

In FIGS. 20 to 21(a) there is illustrated a further wound retractor device 155 according to the invention, which is similar to the device 55 of FIG. 19, and similar elements in FIGS. 20 to 21(a) are assigned the same reference numerals.

In this case the connecting member, which extends between the proximal ring member 4 and the distal ring member 2, is provided in the form of a sleeve member 156 and two strap members 5. The two strap members 5 extend from an end of the sleeve member 156 in the same direction.

The first end 8 of the sleeve member 156 is fixedly attached to the proximal ring member 4, and extends distally towards the distal ring member 2 in the first layer 9. At the distal ring member 2, the sleeve member 156 is looped around the entire distal ring member 2. The two strap members 5 are attached to an end of the sleeve member 5, and extend from the end of the sleeve member 156 proximally to the second end 10 in the second layer 11.

As illustrated in FIG. 20, the two strap members 5 are attached together, in this case with the sleeve member 156 providing the means of attachment.

The circumferential dimension of the sleeve member 156 is substantially equal to the sum of the circumferential dimension of the two strap members 5, as illustrated in FIG. 20.

The wound retractor device 155 is self-locking to maintain the wound opening 3 laterally retracted.

To maintain the wound opening 3 in the retracted configuration the second 10 of each strap member 5 does not have to pass through a slot in the proximal ring member 4, or to be hooked onto the proximal ring member 4, or in any other way to be engaged against the proximal ring member 4. The wound retractor device 155 is self-locking, even when the second ends 10 of the strap members 5 do not engage against the proximal ring member 4.

After lateral retraction of the sides of the wound opening 3, the portion of the second layer 11 of each strap member 5 which is external of the wound opening 3 is redundant. This external portion of each strap member 5 does not contribute to maintaining the wound opening 3 retracted, and may therefore be removed if desired, for example by cutting this external portion.

The second ends 10 of the strap members 5 may be moved in a direction substantially parallel to the longitudinal axis A-A of the wound opening 3 to retract laterally the sides of the wound opening 3, as illustrated in FIGS. 20 and 21.

Alternatively the second ends 10 of the strap members 5 may be moved in a lateral direction to retract laterally the sides of the wound opening 3, as illustrated in FIG. 21(a). In this case, the second ends 10 are moved in a direction substantially perpendicular to the longitudinal axis A-A of the wound opening 3.

Figure 22:
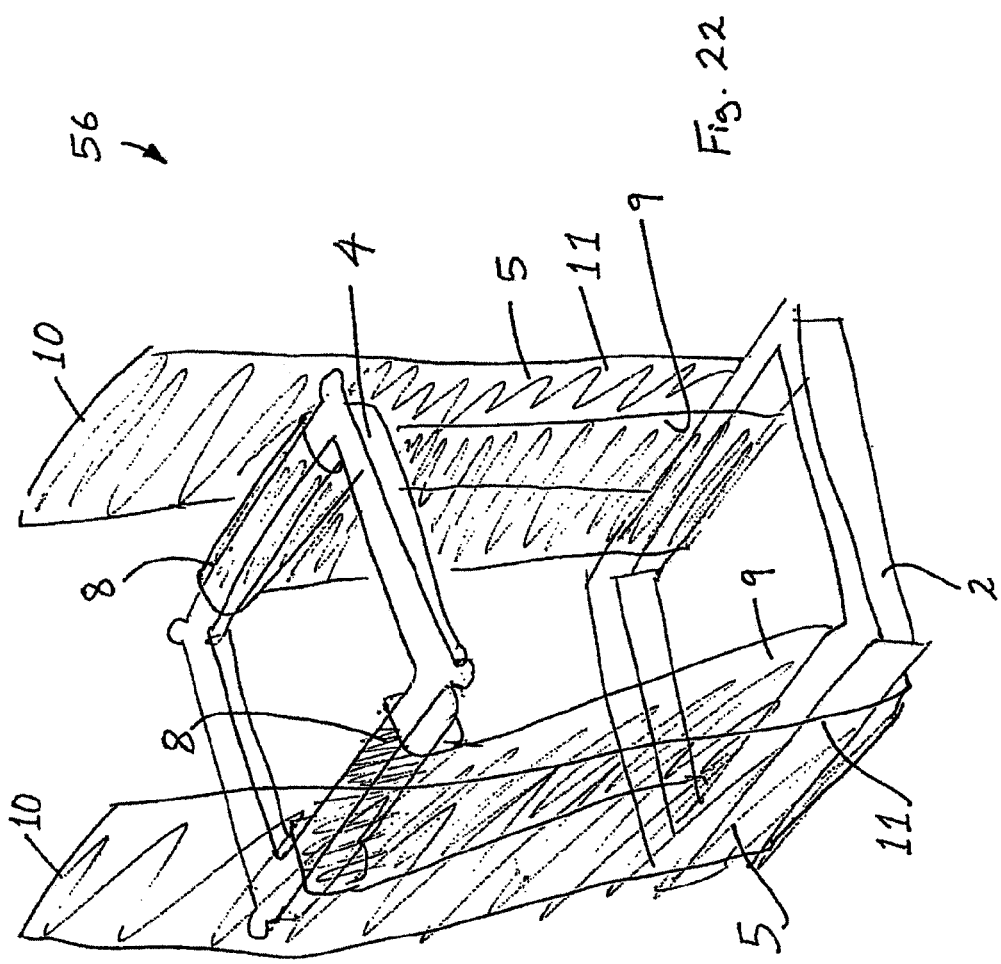
FIG. 22 is a perspective view of a further wound retractor device according to the invention.

Referring to FIG. 22, there is illustrated a further wound retractor device 56 according to the invention, which is similar to the device 55 of FIG. 19, and similar elements in FIG. 22 are assigned the same reference numerals.

In this case, the distal ring member 2 and the proximal ring member 4 are substantially square-shaped. The square shape acts to prevent bunching of, in particular, the distal ring member 2.

It will be appreciated that the distal ring member 2 and/or the proximal ring member 4 may be provided in a variety of different shapes.

It will further be appreciated that hinging means may be provided on the distal ring member 2 to facilitate temporary collapsing of the distal ring member 2 to a lower-profile configuration for ease of insertion into the wound opening 3.

The invention is not limited to the embodiments hereinbefore described, with reference to the accompanying drawings, which may be varied in construction and detail.

The invention claimed is:

1. A wound retractor device, comprising:
   a distal member for insertion into a wound opening;
   a proximal member for location externally of the wound opening;
   a connecting member extending at least between the distal member and the proximal member, at least part of the connecting member being movable relative to the proximal member to shorten the length of the connecting member located between the distal member and the proximal member for retracting laterally sides of the wound opening;
   a guide slot radially extending substantially normal to a longitudinal axis of the proximal member to guide movement of the connecting member relative to the proximal member, through which at least part of the connecting member changes its direction to substantially perpendicular to a longitudinal axis of the wound retractor device and outward substantially normal to the longitudinal axis of the proximal member; and
   a protector separated from the connecting member, wherein the protector is configured to protect the retracted wound opening, being located radially outside the connecting member, and wherein the protector includes a distal member engaging end at the distal member, and an end opposite the distal member engaging end terminating distal of the slot and being configured to extend along a distal end of the proximal member.

2. A device as claimed in claim 1 wherein the connecting member is movable relative to the distal member.

3. A device as claimed in claim 2 wherein the device comprises a guide to guide movement of the connecting member relative to the distal member.

4. A device as claimed in claim 1 wherein the protector comprises a sleeve member configured to line a retracted wound opening.

5. A device as claimed in claim 4 wherein a first end of the sleeve member is fixed to the distal member and a second end of the sleeve member is configured for location externally of a wound opening.

6. A device as claimed in claim 1, wherein the connecting member engages the distal member.

7. A device as claimed in claim 6, wherein the protector includes a circumferential edge at the distal member engaging end, and every portion of the circumferential edge directly contacts the distal member.

8. A wound retractor device, comprising:
- a distal member configured for insertion into a wound opening;
- a proximal member configured for location externally of the wound opening, the proximal member having a radially innermost surface and a radially outermost surface;
- a connecting member extending at least between the distal member and the proximal member, at least part of the connecting member being movable relative to the proximal member to shorten a length of the connecting member between the distal member and the proximal member;
- a guide slot radially extending through the proximal member from the radially innermost surface to the radially outermost surface, and substantially normal to a longitudinal axis of the proximal member to guide movement of the connecting member relative to the proximal member, through which at least part of the connecting member changes its direction to substantially normal to the longitudinal axis of the proximal member and radially outward relative to the longitudinal axis of the proximal member; and
- a protector separated from the connecting member, wherein the protector is configured to protect the retracted wound opening by being positioned radially outside the connecting member.

9. A device as claimed in claim 8, wherein the connecting member includes a retracting portion configured to exert a retracting force laterally against sides of the wound opening.

10. A device as claimed in claim 8, wherein the connecting member directly engages the distal member.

11. A device as claimed in claim 10, wherein the protector includes an edge, and the entire edge directly engages the distal member.

* * * * *